(12) United States Patent
Chan et al.

(10) Patent No.: US 7,273,469 B1
(45) Date of Patent: Sep. 25, 2007

(54) MODIFIED NEEDLE CATHETER FOR DIRECTIONAL ORIENTATION DELIVERY

(75) Inventors: Gregory Waimong Chan, Mountain View, CA (US); Fernando Gonzalez, Campbell, CA (US); Thuhuong Thi Phan, Milpitas, CA (US); Dwight A. Ambat, Fremont, CA (US); Manolo Lumauig, San Jose, CA (US); Mina W. Chow, Campbell, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 265 days.

(21) Appl. No.: 10/749,354

(22) Filed: Dec. 31, 2003

(51) Int. Cl.
*A61M 29/00* (2006.01)

(52) U.S. Cl. .................................. 604/96.01

(58) Field of Classification Search ................ 604/246, 604/22, 41, 523, 533, 164.1, 96.01, 264, 604/158, 164.13, 164.01, 164.03, 85; 606/192, 606/198
See application file for complete search history.

(56) References Cited

U.S. PATENT DOCUMENTS

| | | |
|---|---|---|
| 4,926,860 A | 5/1990 | Stice et al. |
| 5,681,346 A | 10/1997 | Orth et al. |
| 5,702,418 A | 12/1997 | Ravenscroft |
| 5,810,882 A | 9/1998 | Bolduc et al. |
| 5,904,692 A | 5/1999 | Steckel et al. |
| 5,911,706 A | 6/1999 | Estabrook et al. |
| 5,928,200 A | 7/1999 | Thorne et al. |
| 5,964,806 A | 10/1999 | Cook et al. |
| 6,004,330 A | 12/1999 | Middleman et al. |
| 6,013,051 A | 1/2000 | Nelson |
| 6,017,328 A | 1/2000 | Fischell et al. |
| 6,024,727 A | 2/2000 | Thorne et al. |
| 6,045,498 A | 4/2000 | Burton et al. |
| 6,056,726 A | 5/2000 | Isaacson |
| 6,183,442 B1 | 2/2001 | Athanasiou et al. |
| 6,190,352 B1 | 2/2001 | Haarala et al. |
| 6,200,274 B1 | 3/2001 | McNeirney |
| 6,206,930 B1 | 3/2001 | Burg et al. |
| 6,217,554 B1 * | 4/2001 | Green .................... 604/164.01 |
| 6,241,702 B1 | 6/2001 | Lundquist et al. |

(Continued)

FOREIGN PATENT DOCUMENTS

EP 0712614 5/1996

Primary Examiner—Nicholas D. Lucchesi
Assistant Examiner—Christopher D. Koharski
(74) Attorney, Agent, or Firm—Blakely Sokoloff Taylor & Zafman LLP

(57) ABSTRACT

Methods and apparatus for delivering a treatment agent through a percutaneous delivery apparatus are herein disclosed. In some embodiments, an apparatus can include an expandable body with at least one delivery cannula having a lumen therethrough coupled to an exterior portion of the expandable body. The expandable body can be coupled to a delivery assembly with a hub. The delivery cannula can house at least one needle with a protuberance on a distal end. A portion of the hub can house at least one needle with a protuberance on a proximal end. In some embodiments, the protuberance (proximal or distal) can direct the orientation of the needle during an application of treatment agent. In some embodiments, the delivery cannula can include at least one stop for controlling the movement of the needle during an application of treatment agent. In some embodiments, a sheath can be disposed around the delivery cannula.

27 Claims, 17 Drawing Sheets

U.S. PATENT DOCUMENTS

| | | |
|---|---|---|
| 6,260,552 B1 | 7/2001 | Mortier et al. |
| 6,283,947 B1 * | 9/2001 | Mirzaee ..................... 604/264 |
| 6,283,951 B1 | 9/2001 | Flaherty et al. |
| 6,302,870 B1 * | 10/2001 | Jacobsen et al. ............ 604/272 |
| 6,379,319 B1 | 4/2002 | Garibotto et al. |
| 6,398,762 B1 | 6/2002 | Vetter et al. |
| 6,419,701 B1 | 7/2002 | Cook et al. |
| 6,425,887 B1 | 7/2002 | McGuckin et al. |
| 6,435,481 B2 | 8/2002 | Kahlhamer |
| 6,447,523 B1 | 9/2002 | Middleman et al. |
| 6,506,182 B2 | 1/2003 | Estabrook et al. |
| 6,520,983 B1 | 2/2003 | Colgan et al. |
| 6,527,778 B2 | 3/2003 | Athanasiou et al. |
| 6,533,795 B1 | 3/2003 | Tran et al. |
| 6,537,292 B1 | 3/2003 | Lee |
| 6,551,289 B1 | 4/2003 | Higuchi et al. |
| 6,692,466 B1 * | 2/2004 | Chow et al. ............ 604/164.01 |
| 6,770,053 B2 * | 8/2004 | Scarfone et al. ............ 604/117 |
| 6,835,193 B2 * | 12/2004 | Epstein et al. ............... 604/507 |
| 2002/0002349 A1 * | 1/2002 | Flaherty et al. ......... 604/164.11 |
| 2004/0133154 A1 * | 7/2004 | Flaherty et al. ........... 604/93.01 |

* cited by examiner

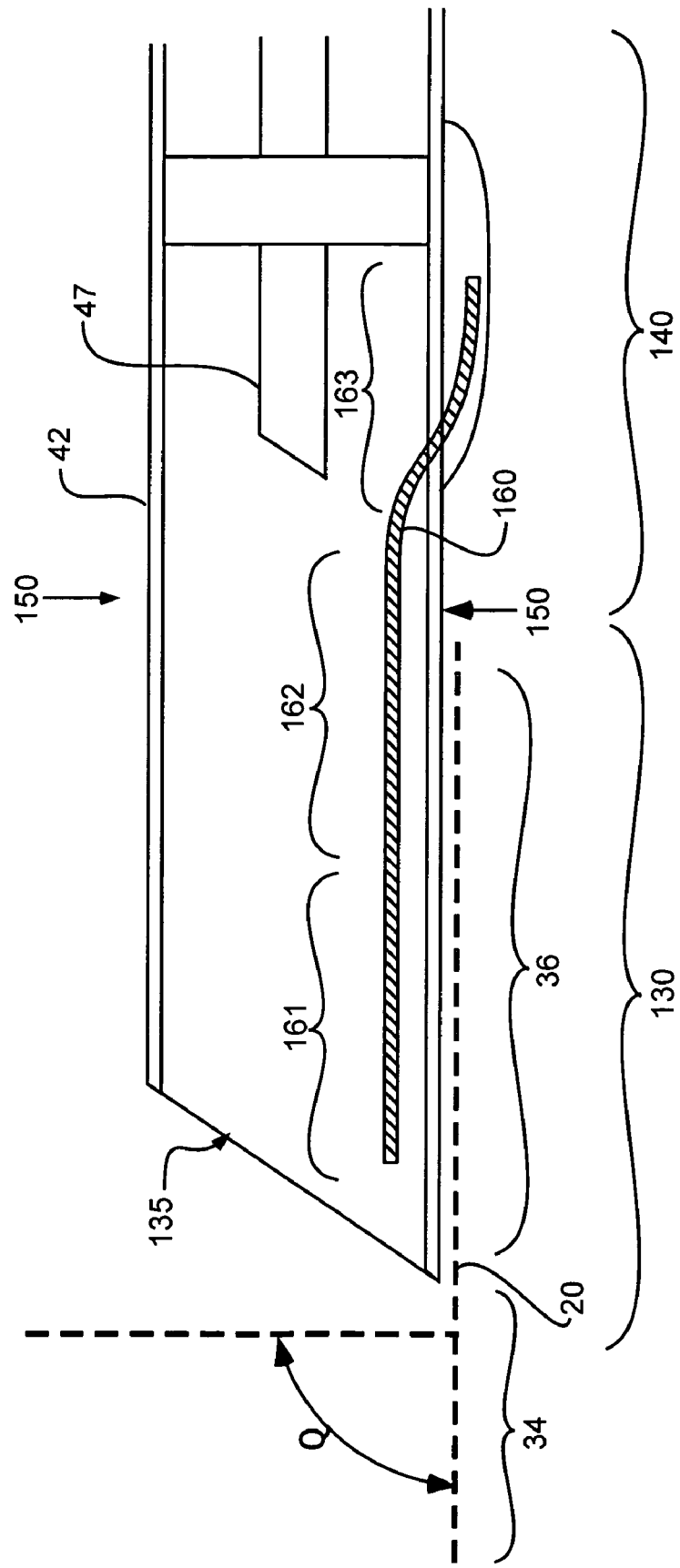

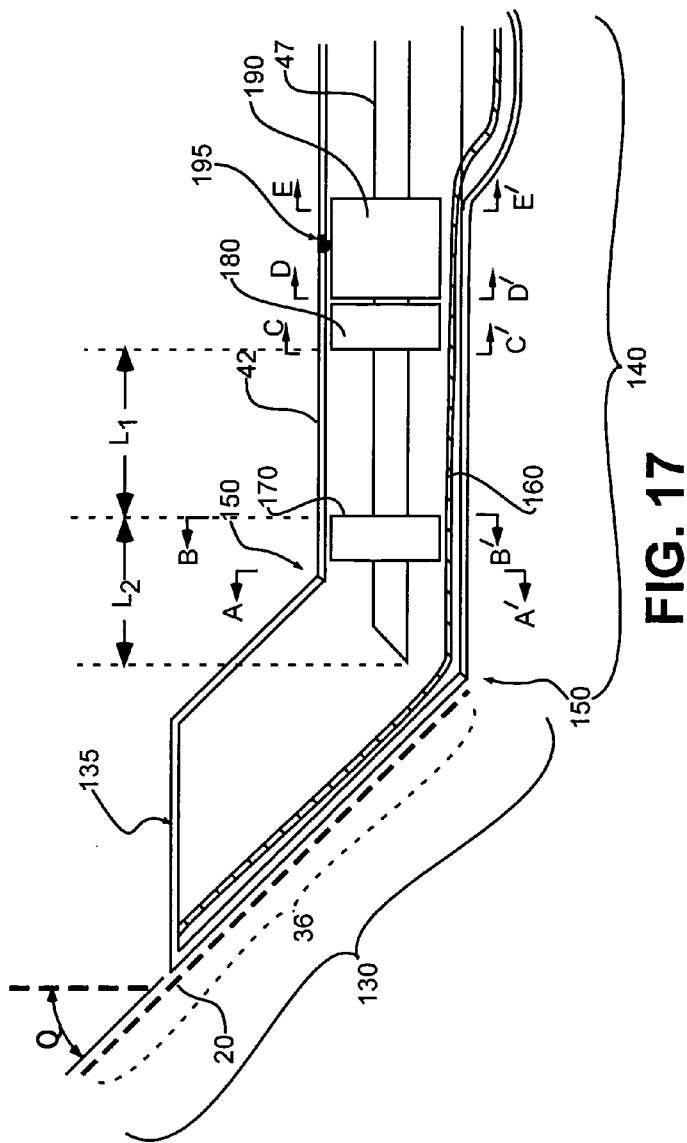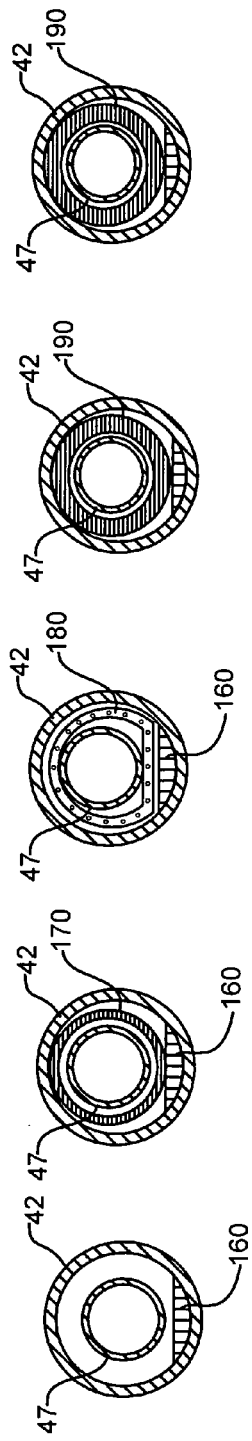

MODIFIED NEEDLE CATHETER FOR DIRECTIONAL ORIENTATION DELIVERY

BACKGROUND

1. Field

Percutaneous delivered medical device.

2. Background

Percutaneous transluminal coronary angioplasty (PTCA) is a procedure for treating heart disease. In a typical procedure, a catheter assembly having a balloon portion is introduced percutaneously into the cardiovascular system of a patient via the brachial or femoral artery. The catheter assembly is advanced through the coronary vasculature until the balloon portion is positioned across an occlusive lesion. Once in position across the lesion, the balloon is inflated to a predetermined size to radially compress the atherosclerotic plaque of the lesion against the inner wall of the artery to dilate the lumen. The balloon is then deflated to a smaller profile to allow the catheter to be withdrawn from the patient's vasculature.

Restenosis of the artery commonly develops over several months after the procedure, which may require another angioplasty procedure or a surgical by-pass operation. Restenosis is thought to involve the body's natural healing process. Angioplasty or other vascular procedures injure the vessel walls, removing the vascular endothelium, disturbing the tunica intima, and causing the death of medial smooth muscle cells. Excessive neoinitimal tissue formation, characterized by smooth muscle cell migration and proliferation to the intima, follows the injury. Proliferation and migration of smooth muscle cells (SMC) from the media layer to the intima cause an excessive production of extra cellular matrices (ECM), which is believed to be one of the leading contributors to the development of restenosis. The extensive thickening of the tissues narrows the lumen of the blood vessel, constricting or blocking blood flow through the vessel.

To reduce the chance of the development of restenosis, therapeutic substances may be administered to the treatment site. For example, anticoagulant and antiplatelet agents are commonly used to inhibit the development of restenosis. In order to provide an efficacious concentration to the target site, systemic administration of such medication however often produces adverse or toxic side effects for the patient. Local delivery is a preferred method of treatment in that smaller total levels of medication are administered in comparison to systemic dosages, but are concentrated at a specific site. Local delivery, thus, produces fewer side effects and achieves more effective results.

One commonly applied technique for the local delivery of a therapeutic substance is through the use of a medicated, implantable prosthesis, one example of which includes a stent. A stent coated with a polymeric carrier, which is impregnated with a therapeutic substance, can be deployed at a selected site of treatment. The polymeric carrier allows for a sustained delivery of the therapeutic substance. A disadvantage associated with the use of medicated stents is that the quantity of the substance that can be impregnated in the polymeric carrier is limited. In order to increase the capacity of the polymeric carrier, the amount of polymeric material employed, the profile (e.g., thickness) of the coating must be increased to accommodate the quantity of the substance used. An increase in the profile of the coating significantly limits the applications for which the stents can be used.

One technique for the local delivery of a therapeutic substance into the tissue surrounding a bodily passageway is disclosed in U.S. Pat. No. 5,464,395 to Faxon et al. U.S. Pat. No. 5,464,395 discloses a catheter including a needle cannula slidably disposed in a needle lumen and a balloon, which is coupled to the distal end of the catheter. When the balloon is inflated, the needle lumen is brought into close engagement with the tissue and the needle cannula can be moved between a position inboard of the catheter distal surface and a position where the needle cannula is projected outboard of the catheter to deliver the therapeutic substance to the tissue.

It has been observed, that in most instances, the inflation and deflation of the balloon causes the needle lumen to form a tortuous pathway, which the needle cannula must traverse to reach the tissue. Unfortunately, under these conditions, the needle cannula can become stuck in the pathway, such that it cannot be advanced. For example, the sharp tip of the needle cannula can gouge, become lodged in, or puncture the catheter wall. Curving the tip of the needle may help to prevent some damage, but it can require that the needle lumen be made undesirably larger to accommodate the curved needle tip and may result in inconsistent needle engagement with the tissue.

SUMMARY

In one embodiment, an apparatus is disclosed. Representatively, an apparatus includes an expandable body having dimensions suitable for percutaneous delivery and at least one delivery cannula connected to an exterior portion of the expandable body. The at least one delivery cannula includes a plication region that is defined in response to an expansion of the expandable body. Further, the apparatus includes a sheath ring disposed about the at least one delivery cannula and the catheter body adjacent the plication region.

An apparatus such as described may be used to provide a treatment agent, including drug therapy, to a distressed, diseased, or otherwise injured or damaged physiological lumen, for example, to prevent or treat arterial restenosis and/or to promote an angiogenic response in an arterial system. Representatively, the apparatus describes a portion of a catheter assembly including a balloon capable of being inflated to selectively dilate from a collapsed configuration to an expanded configuration at a point or region of interest within a physiological lumen such as a blood vessel. The at least one delivery cannula may accommodate a needle for allowing a treatment agent to be delivered through the needle and injected into a tissue of the physiological lumen. The delivery cannula bends or plicates upon the expansion of the expandable body such as a balloon. The sheath ring may be located proximally adjacent to a stress point of the plication region and inhibit the separation of the delivery cannula from the expandable body. Another embodiment may include multiple balloons connected, for example, in series with one or more of the balloons including one or more delivery cannulas. In situations where multiple delivery cannulas are contemplated, the apparatus may include a sheath ring, for example, adjacent a plication region of each delivery cannula.

In another embodiment, an apparatus is also disclosed. The apparatus includes an expandable body such as a balloon having dimensions suitable for percutaneous delivery and at least one delivery cannula having the lumen therethrough connected to an exterior portion of the expandable body. The apparatus also includes a needle disposed in the lumen of the at least one delivery cannula, the needle including a body portion having a protuberance thereon. Further, the apparatus includes a stop disposed in the lumen of the at least one delivery cannula at a position proximal to the protuberance on the needle. The stop defines a diameter of the lumen less than an outer diameter of the needle at the protuberance. In this manner, a needle disposed in the at least one delivery cannula can be retracted only to a point where the protuberance contacts the stop. In another embodiment, the protuberance is a sleeve coupled to the needle and the stop is a sleeve coupled to the delivery cannula. In still another embodiment, an additional stop may be both in the at least one delivery cannula lumen at a position distal to the protuberance on the needle, such that the needle may be advanced only as far as a point where the protuberance contacts the distal stop. In yet a further embodiment, the at least one delivery cannula may include a first cross-sectional shape at a portion proximal to the distal stop that is different from a second cross-sectional shape distal to the second stop. In this manner, an orientation of the needle may be maintained as it is advanced through the at least one delivery cannula to a treatment site. Again, in another embodiment, an apparatus may include multiple expandable bodies (e.g., multiple balloons) within one or more delivery cannulas coupled to one of the expandable bodies or multiple ones of the expandable bodies. Each delivery cannula and needles associated with each delivery cannula may include a protuberance and/or stop(s) as described.

In another embodiment, an apparatus suitable as a needle structure for a catheter assembly is also disclosed. Representatively, the apparatus includes a first cannula body having dimensions suitable for percutaneous delivery through a catheter cannula. The apparatus also includes a second cannula body connected to the first cannula body. The second cannula body includes, in one embodiment, a superelastic material, such as a nickel-titanium alloy. Collectively, the first cannula body and the second cannula define a continuous lumen therethrough. In one embodiment, the second cannula body defines a distal end of a needle structure.

Also, an apparatus including a catheter cannula including at least one needle and a hub is also disclosed. The catheter cannula has a length suitable for tracking through a portion of a vasculature and a dimension suitable for percutaneous delivery. The catheter cannula may include one or more expandable bodies, such as one or more inflatable balloons, at a distal end (e.g., connected in series at a distal end of catheter cannula). The hub is connected to a proximal portion of the catheter cannula. The at least one needle extends through a portion of the catheter cannula and a proximal portion of the needle is associated with the hub. The hub prescribes a radial orientation to the at least one needle. The hub may also limit a proximal and distal travel of the needle.

A method is further disclosed. The method includes positioning a catheter assembly including at least one delivery device disposed in at least one delivery cannula; modifying the shape of the catheter assembly to modify the orientation of the exit end of the at least one delivery cannula at a region of interest; and advancing the at least one needle delivery device beyond the exit end of the at least one delivery cannula according to a controlled orientation of the at least one delivery device within the at least one delivery lumen.

Various features of the apparatuses and methods described are discussed in commonly-owned U.S. patent application Ser. No. 09/746,498, filed Dec. 21, 2000, titled "Local Drug Delivery Catheter with Retractable Needle"; and U.S. patent application Ser. No. 10/394,834, filed Mar. 20, 2003, titled "Drug Delivery Catheter with Retractable Needle." Each of these applications is incorporated herein in their entirety.

Additional features, embodiments, and benefits will be evident in view of the figures and detailed description presented herein.

BRIEF DESCRIPTION OF THE DRAWINGS

Features, aspects, and advantages of embodiments of the invention will become more thoroughly apparent from the following detailed description, appended claims, and accompanying drawings in which:

FIG. 16 shows a distal portion of a delivery cannula of the catheter assembly of FIG. 1 when a balloon of the catheter assembly is in a deflated state.

FIG. 17 shows the portion of the delivery cannula of FIG. 8 when a balloon is in an inflated state and a needle in the delivery cannula is in a retracted state.

FIG. 18 shows a cross-sectional side view through line A-A' of FIG. 17.

FIG. 19 shows a cross-sectional side view through line B-B' of FIG. 17.

FIG. 20 shows a cross-sectional side view through line C-C' of FIG. 17.

FIG. 21 shows a cross-sectional side view through line D-D' of FIG. 17.

FIG. 22 shows a cross-sectional side view through line E-E' of FIG. 17.

DETAILED DESCRIPTION

Figure 1:
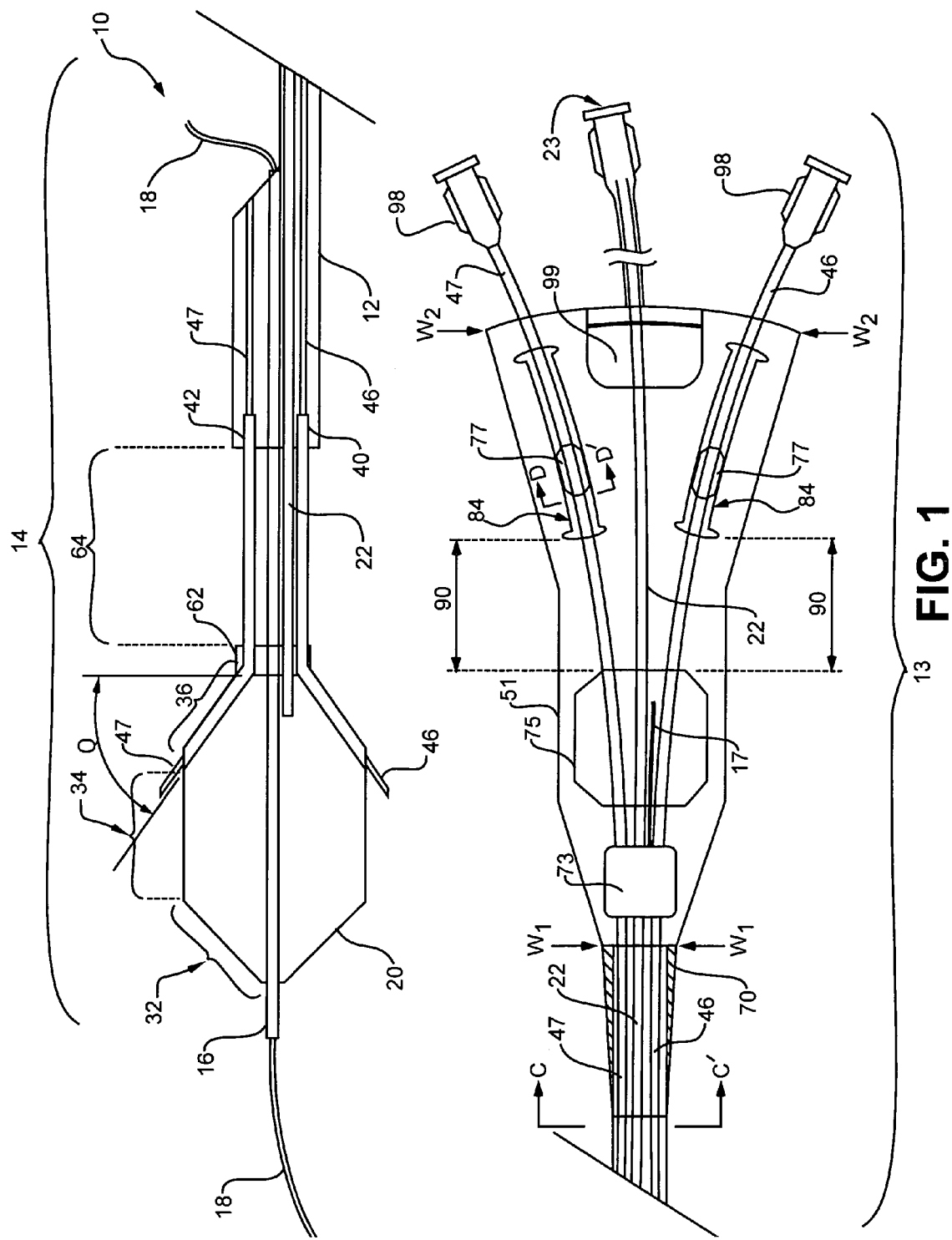
FIG. 1 is a simplified sectional side view of an embodiment of a catheter assembly having a balloon and a therapeutic substance delivery assembly.

FIG. 1 illustrates a catheter assembly or apparatus. In one embodiment, the catheter assembly provides a method for delivering a treatment agent, such as a therapeutic agent or substance or a combination of therapeutic agents or substances, to or through a desired area defining a physiological lumen in order to treat a localized area defining the lumen or to treat a localized area of tissue located adjacent to the lumen. Catheter assembly 10 is intended to broadly include any medical device for insertion into a physiological lumen to permit injection and/or withdrawal of fluids, to maintain patency of the lumen or the area defining the lumen, or for other purposes. It is comtemplated that the catheter assembly has applicability for use with any physiological lumen, including blood vessels, urinary tract, intestinal tract, kidney ducts, wind pipes, and the like.

In one embodiment, catheter assembly 10 includes catheter body 12 having proximal portion 13 and distal portion 14. Catheter assembly 10 includes guidewire cannula 16 for allowing catheter assembly 10 to be fed and maneuvered over guidewire 18. In one embodiment, guidewire cannula 16 extends the length of catheter body 12 from proximal portion 13 to distal portion 14. Representatively, in a typical procedure, guidewire 18 may be initially placed through a region of interest in a physiological lumen (e.g., a blood vessel) and catheter body 12 is advanced on/over guidewire 18 to or through a region of interest in an over the wire (OTW) fashion. In another embodiment, illustrated in FIG. 1, catheter assembly 10 is a rapid exchange (RX) type catheter assembly and only a portion of catheter assembly 10 (a distal portion) is advanced over guidewire 18. It is appreciated that guidewire 18 may be retracted or removed once catheter assembly 10 is placed at a region of interest.

In the embodiment of FIG. 1, catheter assembly 10 includes balloon 20 incorporated at distal portion 14 of catheter assembly 10. Balloon 20 is an expandable body in fluid communication with inflation cannula 22 disposed within catheter body 12. Inflation cannula 22 extends from balloon 20 within distal portion 14 to inflation port 23 within proximal portion 13 (e.g., at a proximal end of catheter assembly 10).

In the embodiment shown in FIG. 1, balloon 20 is in an expanded or inflated state. Balloon 20 is selectively inflatable to dilate from a collapsed configuration to a desired and controlled expanded configuration. Balloon 20 can be selectively inflated by supplying a fluid (e.g., liquid) into inflation cannula 22 at a predetermined rate of pressure through inflation port 23. Likewise, balloon 20 is selectively deflatable to return to a collapsed configuration or a deflated profile.

In one embodiment, balloon 20 can be defined by three portions: distal taper wall 32, medial working length 34, and proximal taper wall 36. In one embodiment, proximal taper wall 36 can taper at any suitable angle θ, typically between about 15° to less than about 90°, when balloon 20 is in an expanded (inflated) configuration.

Balloon 20 can be made from many suitable material, including, but not limited to, polymers and copolymers of polyolefins, polyamides, polyester and the like. The specific material employed should be compatible with inflation or expansion fluid and must be able to tolerate the pressures that are developed within balloon 20. One suitable material is an elastomeric nylon such as PEBAX™, a condensation polymerized polyether block polyamide. PEBAX™ is a trademark of ATOCHEM Corporation of Puteaux, France. Other suitable materials for balloon 20 include, but are not limited to, a biocompatible blend of polyurethane and silicone, or a styrenic block copolymer (SBC) or blend of SBCs. Distal taper wall 32, medial working length 34, and proximal taper wall 36 can be bound together by seams or be made out of a single seamless material. A wall of balloon 20 (e.g., at any of distal taper wall 32, medial working length 34 and/or proximal taper wall 36) can have any suitable thickness so long as the thickness does not compromise properties that are critical for achieving optimum performance. Relevant properties include, but are not limited to, high burst strength, low compliance, good flexibility, high resistance to fatigue, the ability to fold, the ability to cross and recross a desired region of interest or an occluded region in a physiological lumen and low susceptibility to defects caused by handling. By way of example, not limitation, a suitable thickness of a balloon wall can be in the range of about 0.0005 inches to 0.002 inches, the specific specifications depending on the procedure for which balloon 20 is to be used and the anatomy and size of the target lumen in which balloon 20 is to be inserted.

Balloon 20 may be inflated by the introduction of a fluid (e.g., liquid) into inflation cannula 22 (through inflation port 23 at a point outside the physiological lumen). Liquids containing therapeutic and/or diagnostic agents may be used to inflate balloon 20. In one embodiment, balloon 20 may be made of a material that is permeable to such therapeutic and/or diagnostic agents. To inflate balloon 20, a suitable fluid may be supplied into inflation cannula 22 at a predetermined pressure, for example, between about 1 and 20 atmospheres (atm). A specific pressure depends on various factors, such as the thickness of balloon wall 30, the material from which balloon wall 30 is made, the type of substance employed, and the flow rate that is desired.

In another embodiment, balloon 20 is a material that may be inflated under low pressure conditions or with a fixed volume of a fluid including liquid or air. Representatively, where balloon 20 is used as a mechanism to deliver a delivery cannula and needle to a treatment site, concerns of, for example, dilating a blood vessel, are not significant. Thus, balloon 20 may be an elastomeric material that may be inflated by air (e.g., relatively low air pressure) in a volume controlled environment.

Catheter assembly 10, in the embodiment shown in FIG. 1 also includes delivery cannula 40 and delivery cannula 42 each connected to proximal taper wall 36 of balloon 20 and extending at a proximal end, in one embodiment, into a portion of catheter body 12 of catheter assembly 10. Representatively, a suitable length for delivery cannula 40 and delivery cannula 42 is on the order of three to 6.5 centimeters (cm). Delivery cannula 40 and delivery cannula 42 can be made from any suitable material, such as polymers and copolymers of polyamides, polyolefins, polyurethanes, and the like. Catheter assembly 10 also includes needle 46 and needle 47. Needle 46 and needle 47 extend from distal portion 14 to proximal portion 13 of catheter assembly 10. At distal portion 14, needle 46 is disposed through a lumen of delivery cannula 40 and needle 47 is disposed through a lumen of delivery cannula 42. Thus, a dimension of delivery cannula 40 and delivery cannula 42 are each selected to be such to allow a delivery device such as a needle to be moved therethrough. Representatively, delivery cannula 40 has an inner diameter (lumen diameter) on the order of 0.0155 inches and an outer diameter on the order of 0.0255 inches. In the illustrated embodiment, two needles are shown with catheter assembly 10. Delivery cannula 40 and delivery cannula 42 may be spaced either radially and/or circumferentially from each other, for example, between 45° and 180° apart. In other embodiments, a catheter assembly may include fewer needles (e.g., one needle) or more needles (e.g., greater than two). In multiple (two or more) needle assemblies, the needles may be oriented with respect to one another according, representatively, to the purpose sought to be achieved by the delivery assembly. Representatively, needles may be placed adjacent to one another or circumferentially spaced around a proximal taper wall of a balloon.

FIG. 1 shows delivery cannula 40 and delivery cannula 42 each connected to an exterior surface of balloon 20. Specifically, a distal end of each of delivery cannula 40 and delivery cannula 42 extend to a point equivalent to or less than a length of proximal taper wall 36 of balloon 20. One suitable technique for connecting delivery cannula 40 or delivery cannula 42 to balloon 20 is through an adhesive. A suitable adhesive includes a cyanocrylate (e.g., LOCTITE 414™) adhesive, particularly where the balloon material is a PEBAX™ material.

Catheter assembly 10 in the embodiment shown in FIG. 1 also includes sheath ring 62. Sheath ring 62 is positioned over, in this embodiment, guidewire cannula 16, inflation cannula 22, delivery cannula 40, and delivery cannula 42. In one embodiment, sheath ring 62 functions to inhibit delamination of delivery cannula 40 and delivery cannula 42 from proximal taper wall 36 of balloon 20. Thus, a distal end of sheath ring 62 is placed, in one embodiment, at a point immediately proximal to where a delivery cannula will rotate, bend or plicate in response to the expansion or inflation of balloon 20.

Figure 2:
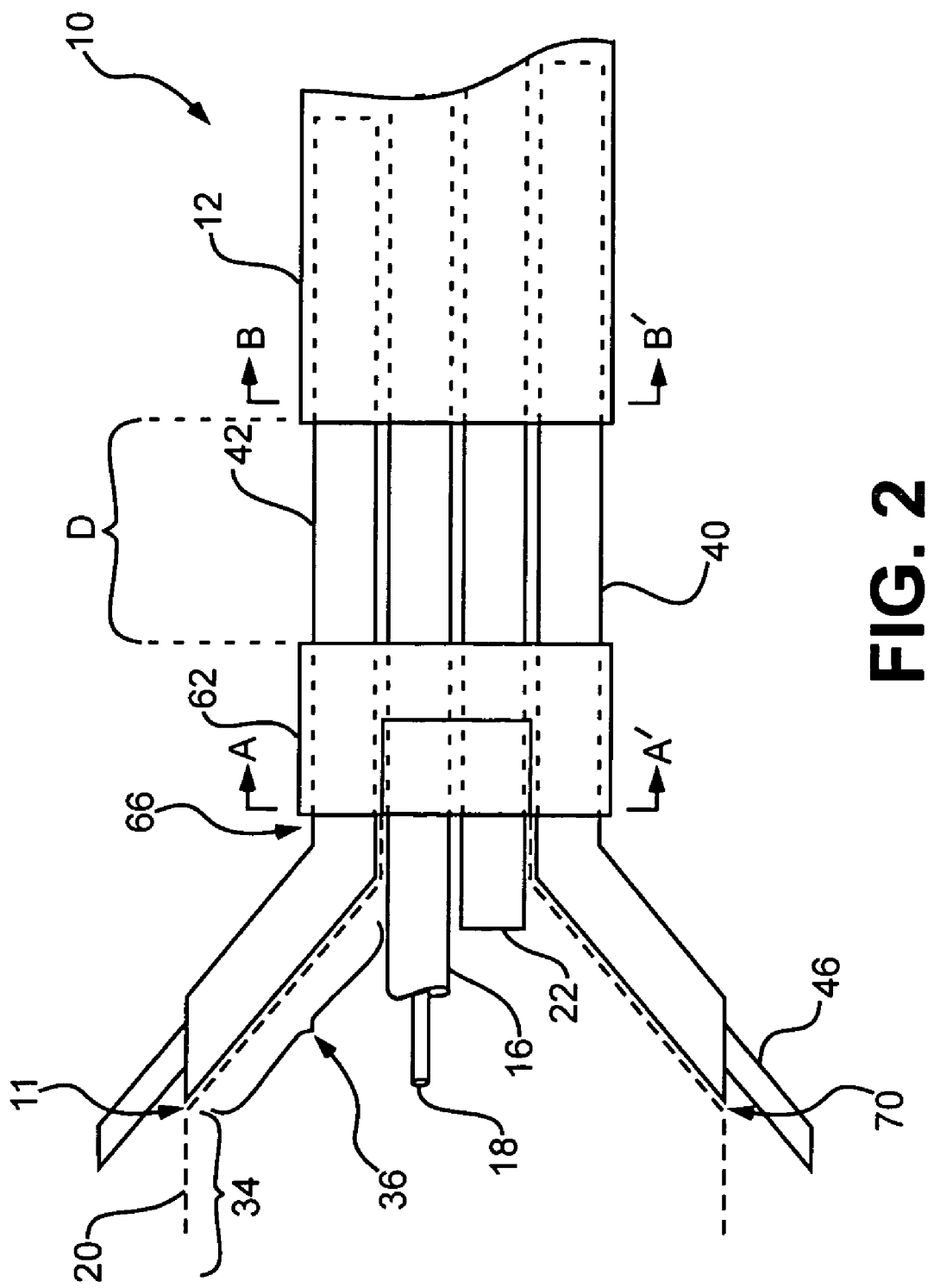
FIG. 2 shows a magnified view of a portion of the catheter assembly of FIG. 1 at a proximal side of the balloon.

FIG. 2 shows a magnified view of a portion of catheter assembly 10 of FIG. 1. Specifically, FIG. 2 shows a portion of catheter assembly 10 including the distal end of catheter body 12 and sheath ring 62. FIG. 2 also shows a portion of balloon 20, including proximal taper wall 36 and medial working length 34. According to one embodiment, delivery cannula 40 and delivery cannula 42 are each connected to (bonded to) proximal taper wall 36 through an adhesive. Sheath ring 62 includes a body having a lumen therethrough suitable to accommodate, in this embodiment, first delivery cannula 40, second delivery cannula 42, guidewire cannula 16 and inflation cannula 22. A lumen of sheath ring 62 also accommodates a proximal portion of balloon 20.

In one embodiment, sheath ring 62 is a biocompatible material that is capable of connecting to (e.g., bonding to) a material for balloon 20 and to a material for each of the noted cannulas that it surrounds. One suitable material is a polymer material similar to one or more of the cannulas and/or balloon 20. An example of a suitable material is PEBAX 40D™ tubing material having an inner diameter of 0.046 inches and an outer diameter of 0.050 inches. Representatively, a body of sheath ring 62 has a length from a proximal end to a distal end on the order of 0.25 millimeters (mm) to 0.75 mm, such as 0.5 mm. In the embodiment shown in FIG. 2, a distal end of sheath ring 62 is positioned at point 66 proximally adjacent to a determined plication or bend or rotation point of delivery cannula 40 and delivery cannula 42. Representatively, a distal edge of sheath ring 62 is as close as possible to a determined plication or bend or rotation point of delivery cannula 40 and delivery cannula 42 as possible. Point 66, in one embodiment, is 0.25 millimeters (mm) to 0.5 mm from plication or bend or rotation point of delivery cannula 40 and delivery cannula 42. In another embodiment, point 66 is 0.5 mm from plication or bend or rotation point of delivery cannula 40 and delivery cannula 42. In the embodiment shown in FIG. 2, a proximal end of sheath ring 62 is separated from a distal end of catheter body 12 by gap, D, of, for example, 0.5 mm to 1.5 mm. In one aspect, a gap D between sheath ring 62 and catheter body 12 provides flexibility at a distal end of catheter assembly 10. In another embodiment, there may no gap (D=0) between sheath ring 62 and catheter body 12.

One way to form catheter assembly 10 including sheath ring 62 is to initially connect (e.g., bond) balloon 20 at a distal end to guidewire cannula 16. Balloon 20 is also connected (e.g., bonded) at a proximal end to guidewire cannula 16 and inflation cannula 22. One way to connect balloon 20 at a distal end to guidewire cannula 16 and at a proximal end to guidewire cannula 16 and inflation cannula 22 is through a thermal seal (e.g., heat fusion). Representatively, mandrels may be placed in lumens of guidewire cannula 16 and inflation cannula 22, respectively. A removable shrink wrap may be placed on the exterior of balloon 20 at the connection points to control an outside diameter during a thermal treatment. Next, heat is applied to fuse the materials (e.g., guidewire cannula 16, inflation cannula 22, and balloon 20) together at the connection points and seal the ends of balloon 20. Once fused, the mandrels and the shrink wrap may be removed.

Once balloon 20 is sealed at each end, balloon 20 is inflated. Delivery cannula 40 and delivery cannula 42 are aligned on inflated balloon 20 with a distal end at reference point 11 corresponding to a distal end of proximal taper wall 36 of balloon 20. Distal ends of delivery cannula 40 and delivery cannula 42 may be tapered to approximate or match a plane defined by medial working length 34 of balloon 20 when balloon 20 is in an inflated state. Delivery cannula 40 and delivery cannula 42 may then be glued or affixed to balloon 20 through an adhesive such as a cyanoacrylate adhesive. Next, sheath ring 62 is loaded (advanced proximal to distal) onto a proximal end of balloon 20 and the cannulas of catheter assembly 10 (e.g., guidewire cannula 16, inflation cannula 22, delivery cannula 40 and delivery cannula 42). A material of sheath ring 62 of a polymer such as PEBAX 40D™ may be connected to balloon 20 and delivery cannula 40 and delivery cannula 42 by a thermal seal process such as described above. Representatively, mandrels may be placed in delivery cannula 40, delivery cannula 42 and possibly guidewire cannula 16 and inflation cannula 22. A removable shrink wrap material may be placed over sheath ring 62 and a portion of balloon 20 and adjacent portions of delivery cannula 40, delivery cannula 42, guidewire cannula 16, and inflation cannula 22. The assembly may be heated at sheath ring 62 to fuse sheath ring to delivery cannula 40, delivery cannula 42 and balloon 20 (e.g., 60° C. for 10 minutes for PEBAX 40D). After the thermal seal process, the mandrels and shrink wrap may be removed. As an alternative to a thermal seal process for connecting sheath ring 62, sheath ring 62 may be connected to balloon 20, delivery cannula 40 and delivery cannula 42 by an adhesive, such as cyanoacrylate adhesive.

Figure 3:
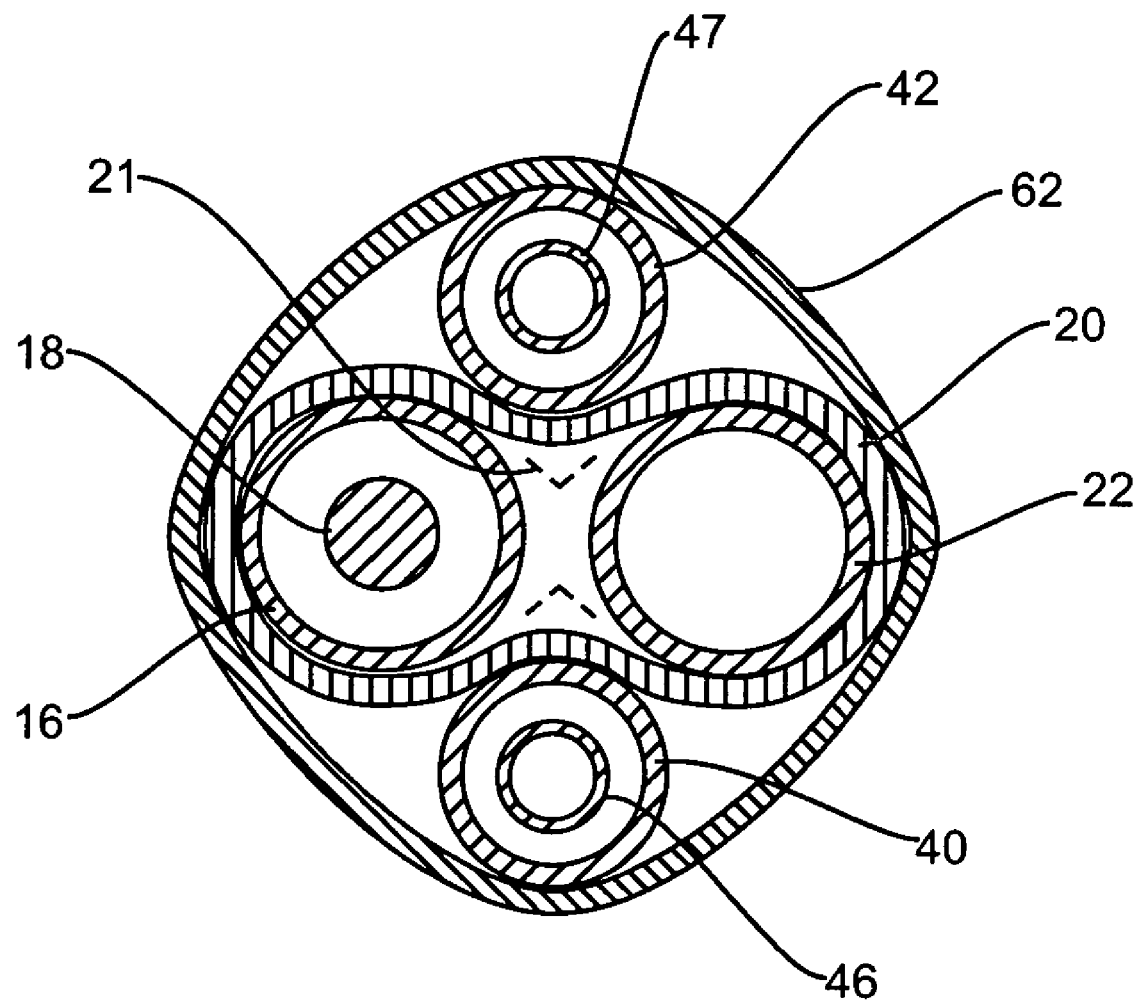
FIG. 3 shows a cross-sectional side view through line A-A' of FIG. 2.

FIG. 3 shows a cross-sectional side view through line A-A' of FIG. 2. FIG. 3 shows sheath ring 62 as a cannula including in a lumen therethrough a proximal portion of balloon 20 and delivery cannula 40 and delivery cannula 42. Disposed within a lumen of delivery cannula 40 is needle 46. Disposed within a lumen of delivery cannula 42 is needle 47. Proximal portion of balloon 20 also defines a lumen including guidewire cannula 16 and inflation cannula 22 disposed therein. Guidewire cannula 16 includes guidewire 18. FIG. 3 shows balloon 20 fused to guidewire cannula 16 and inflation cannula 22 to seal a proximal end of balloon 20. In one embodiment, to ensure a seal, optional filler material 21 of, for example, a suitable polymer material may be placed in gaps between the cannulas.

FIG. 3 also shows delivery cannula 40 and delivery cannula 42 abutting against balloon 20 to minimize the spacing between the cannulas and balloon 20. Thus, in one embodiment, sheath ring 62 collects delivery cannula 40 and delivery cannula 42 in a minimal cross-sectional area. Where sheath ring 62 is fused to balloon 20, delivery cannula 40 and delivery cannula 42, sheath ring 62 adopts a cross-sectional shape consistent with the shape of articles it surrounds. Where sheath ring 62 is glued to balloon 20, delivery cannula 40, and delivery cannula 42, a cross-sectional shape of sheath ring 62 is, for example, circular.

As an alternative to a separate sheath ring, in another embodiment, a distal end of catheter body 12 may be disposed proximally adjacent plication or bend point 66 (see FIG. 2). For example, a distal portion of catheter body 12 may be fused to delivery cannula 40, delivery cannula 42, and balloon 20 in the same manner and according to a similar technique as described with respect to sheath ring 62.

Figure 4:
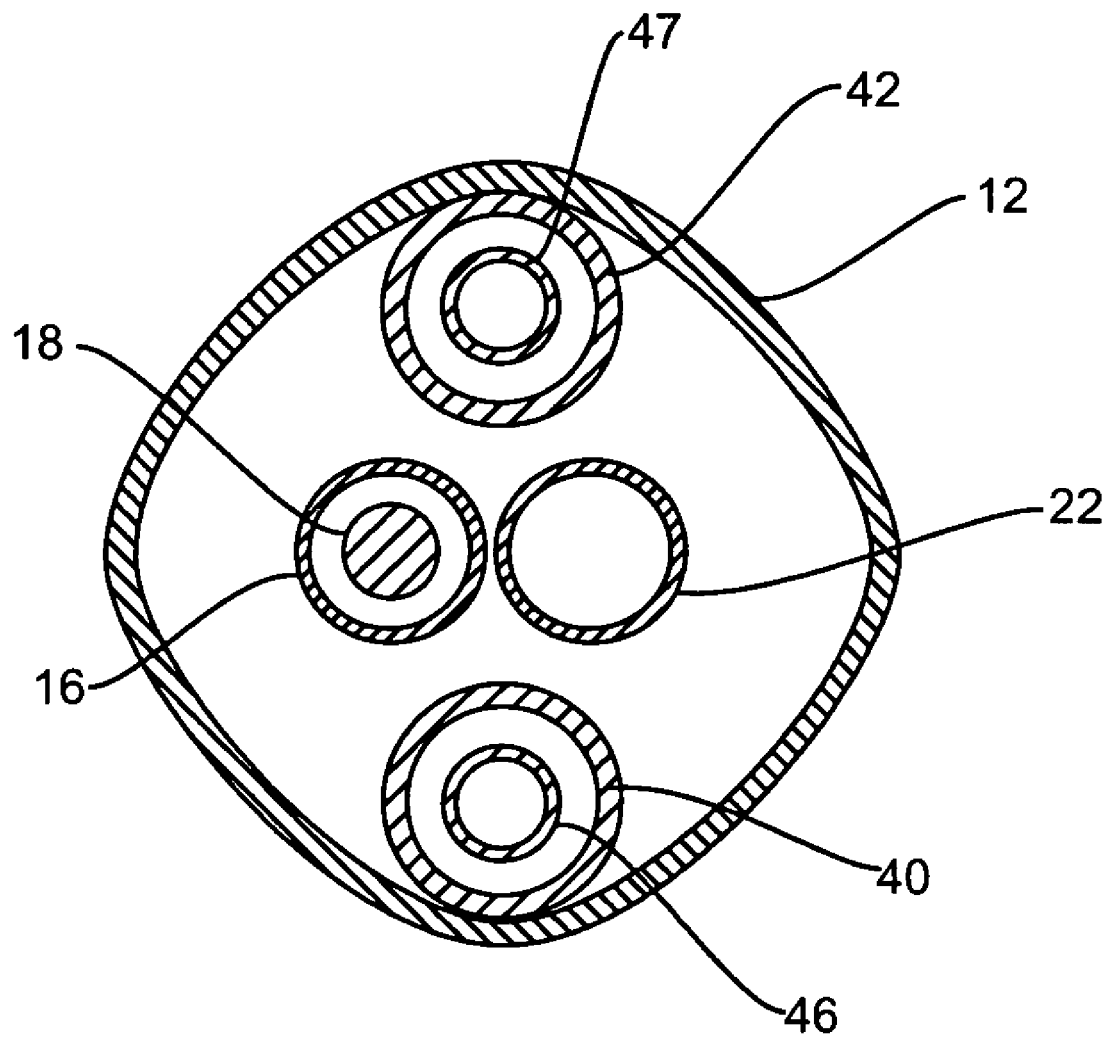
FIG. 4 shows a cross-sectional side view through line B-B' of FIG. 2.

FIG. 4 shows a cross-section through line B-B' of FIG. 2. FIG. 4 shows catheter body 12 as a cannula including a lumen therethrough. Inside the lumen of catheter body 12 is delivery cannula 40 and delivery cannula 42. In a lumen of delivery cannula 40 is needle 46. In a lumen of delivery cannula 42 is needle 47. Also disposed in a lumen of catheter body 12 is inflation cannula 22 and guidewire cannula 16. Disposed within a lumen of guidewire cannula 16 is guidewire 18. In one embodiment, at line B-B', delivery cannula 40 and delivery cannula 42 are not confined to a minimal cross-sectional area as may be the case at line A-A' within sheath ring 62 (see FIG. 3).

Figure 5:
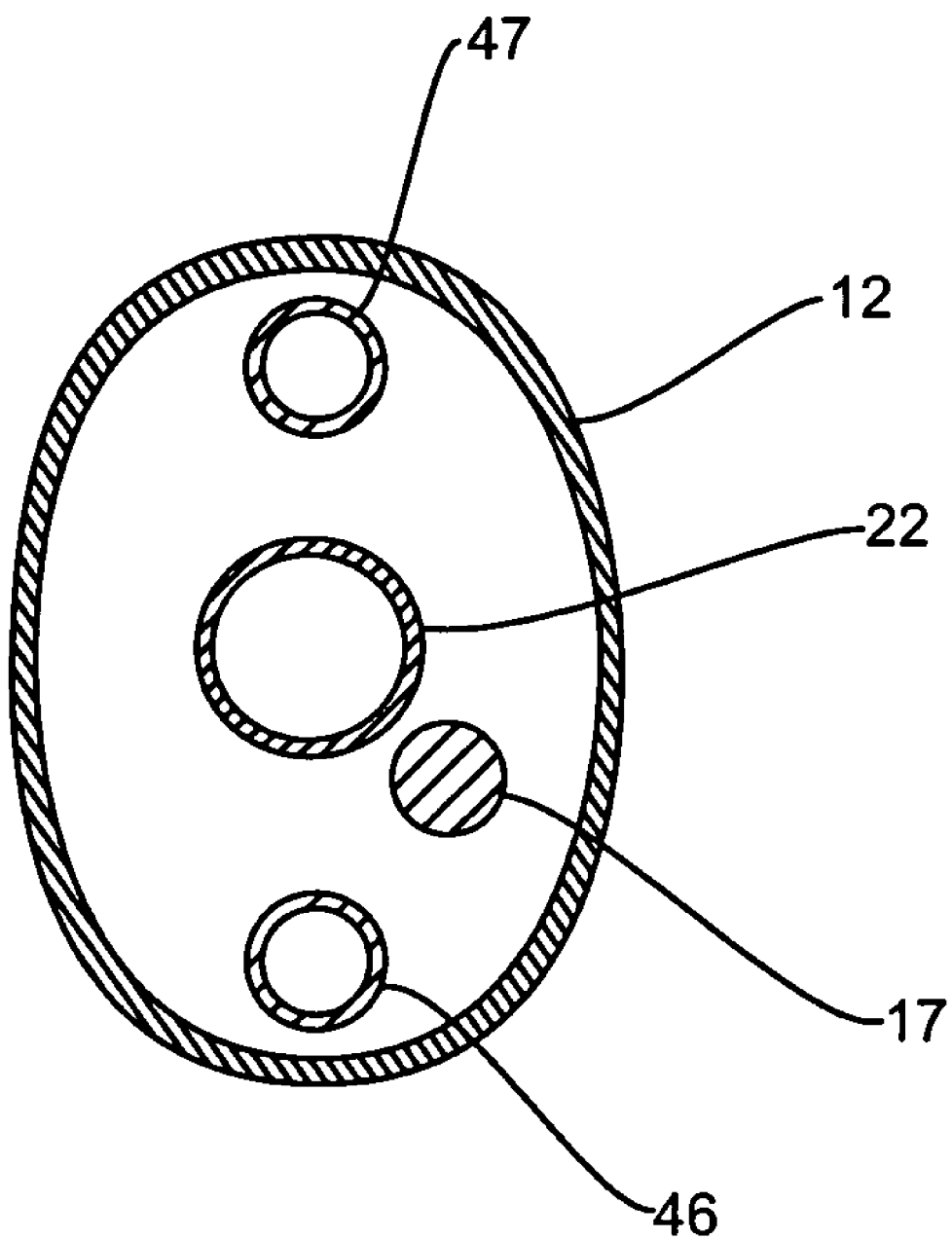
FIG. 5 shows a cross-sectional side view through line C-C' of FIG. 1.

FIG. 5 shows a cross-section through line C-C' of FIG. 1, illustrating a cross-section through a portion of proximal portion 13 of catheter assembly 10. FIG. 5 shows catheter body 12 having a lumen therethrough. Disposed within the lumen of catheter body 12 is needle 46 and needle 47. A lumen of catheter body 12, at this cross-section, also includes inflation cannula 22. It is appreciated that the cross-sectional area of catheter body 12 may be minimized (minimum profile) at proximal portion 13 of catheter assembly 10 because fewer articles are accommodated in a lumen of catheter body 12. FIG. 5 also shows optional support mandrel 17 that may extend from a proximal end of catheter assembly 10 to a point near a proximal end of guidewire cannula 16 in a rapid transfer type catheter assembly such as illustrated in FIG. 1 to provide structural support to proximal portion 13.

Referring again to FIG. 1, proximal portion 13 of catheter assembly 10 is intended, in one embodiment, to reside outside a patient while the remainder of catheter assembly 10 is percutaneously introduced into, for example, the cardiovascular system of a patient via the brachial or femoral artery. In this embodiment, proximal portion 13 of catheter assembly 10 includes hub 51. Hub 51 includes needle 46, needle 47, and inflation cannula 22. In one embodiment, relative to the materials for the various cannulas described, a housing of hub 51 is a hard or rigid polymer material, e.g., a polycarbonate or acrylonitrile butadiene styrene (ABS). A distal end of hub 51 has an opening to accommodate a proximal end of catheter body 12. Hub 51 also has a number of cavities at least partially therethrough (extending in a distal to proximal direction) to accommodate needle 46, needle 47, inflation cannula 22 and support mandrel 17. A proximal portion of hub 51 flares to separate a spacing between needle 46, needle 47, and inflation cannula 22 (i.e., a distal end of hub 51 has a width, W1 sufficient to accommodate a proximal end of catheter body 12 and a proximal end has a width, W2 that is greater than W1).

Figure 6:
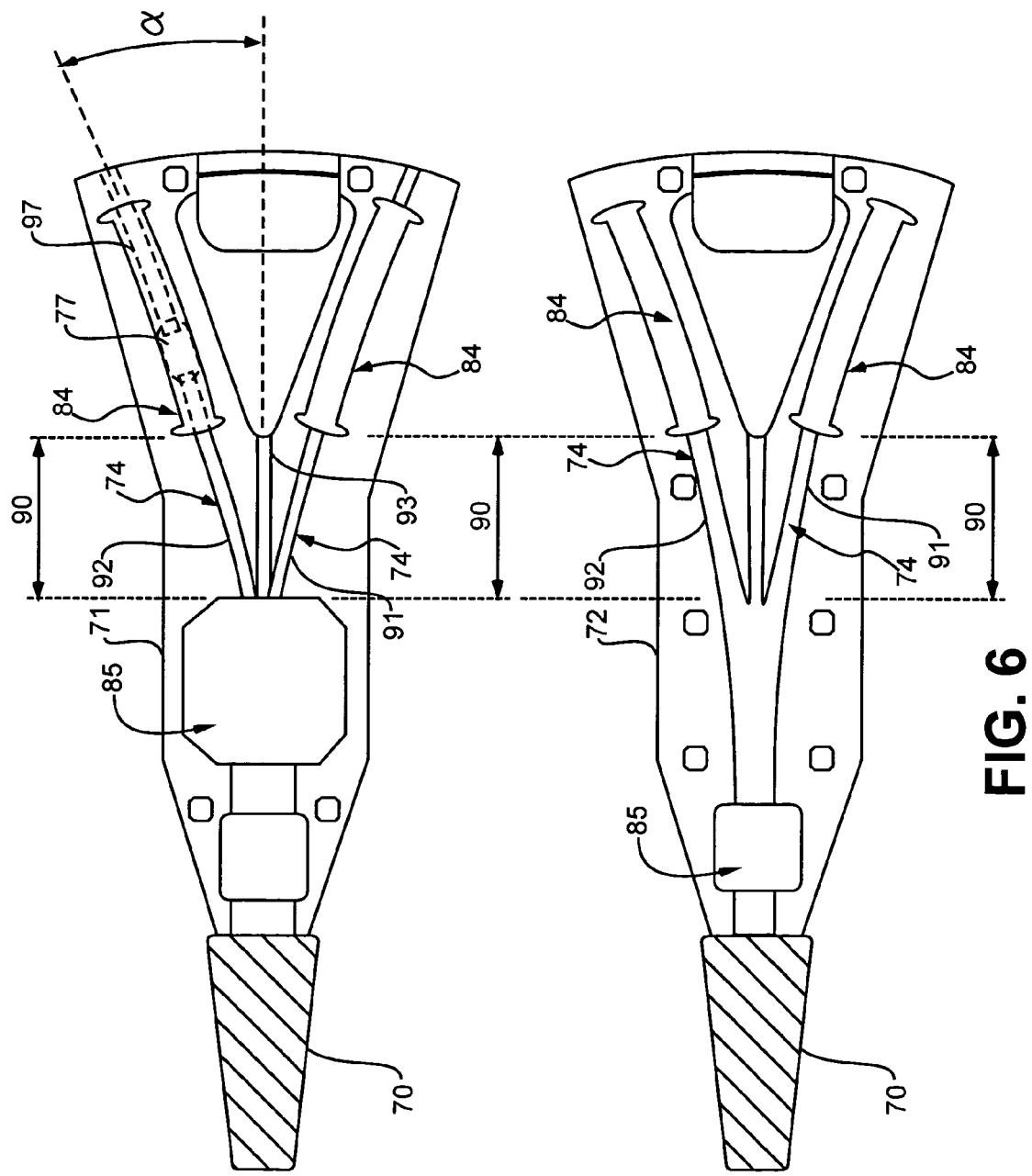
FIG. 6 shows a bisection of a hub of the catheter assembly of FIG. 1 including an interior plan view of two housing halves of the hub.

In one embodiment, hub 51 has at least two functions: needle movement control and balloon inflation and deflation. FIG. 6 illustrates an embodiment of hub 51 as a clamp shell design. With reference to FIG. 1 and FIG. 6, in this embodiment, hub 51 includes the following components: strain relief 70; first housing half 71 and second housing half 72; catheter holder 73 (see FIG. 1 and FIG. 7); track 91 and track 92; cover plate 75 (see FIG. 1 and FIG. 8); needle support tubes 97 (see FIG. 6, FIG. 9 and FIG. 10); sliders 77 (see FIG. 9); inflation cannula holder 99 (see FIG. 1); balloon inflation port 23; and delivery ports 98. A proximal end of catheter body 12 terminates inside hub 51 near a distal end of hub 51. Needle 46, needle 47, inflation cannula 22 extend proximally beyond a proximal end of catheter body 12 and may be secured in respective cavities (described below). A support mandrel 17 may optionally be present at a proximal end of catheter body 12 and may likewise extend proximally beyond the proximal end or may terminate at the distal end of the housing of the hub.

FIG. 1 and FIG. 6 show a distal portion of hub 51 including strain relief 70. Strain relief 70 is an elastic tubular component that may act to reduce stress and inhibit shaft (catheter body 12) kinking for the transition of needle 46, needle 47, and inflation cannula 22 from catheter body 12 to hub 51. A suitable material for strain relief 70 is an elastic polymer material such as SANTOPRENE™. Proximal to strain relief 70 is first housing half 71 and second housing half 72 of similar exterior dimensions that come together to form hub 51. Representatively, strain relief 70 is adhesively bonded to each of first housing half 71 and second housing half 72 (e.g., strain relief 70 of a unitary body may be bonded at a proximal end to a distal end of first housing half 71 and second housing half 72 when the housing halves are connected together).

In the embodiment shown in FIG. 1 and FIG. 6, a housing of hub 51 is in two halves (first housing half 71 and second housing half 72). Where the housing of hub 51 is a plastic or polymer material such as a polycarbonate or an ABS material, an interior of hub 51 may include a number of cavities to secure different components as well as to guide needle movement. First housing half 71 and second housing half 72 may be assembled together (mated) using screw fasteners (illustrated), glue, or plastic bonding techniques such as ultrasonic welding (e.g., thermal bonding). The individual housing halves when made of a plastic or polymer material may be formed, according to conventional molding techniques.

Figure 7:
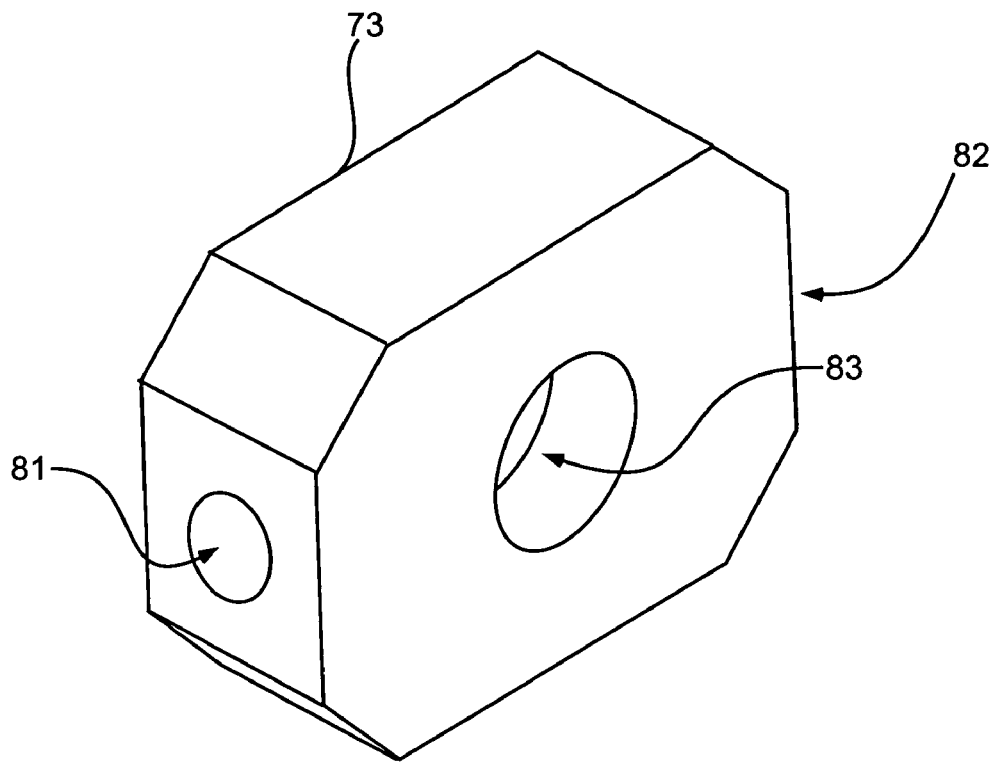
FIG. 7 shows a top and side perspective view of a catheter holder in the housing of the hub of the catheter assembly of FIG. 1.

Inside housing halves (first housing half 71 and second housing half 72) of hub 51, a proximal end of catheter body 12 is secured and oriented within catheter holder 73 by, for example, gluing or heat bonding a proximal end of catheter body 12 within an opening of catheter holder 73. FIG. 7 shows a perspective distal side view of catheter holder 73. In this embodiment, catheter holder 73 is, for example, a plastic material of a polycarbonate, NYLON™, or an ABS material in the shape of a rectangular cube having dimensions suitable to nest within a housing of hub 51. Representative dimensions for catheter holder 73 of a polycarbonate material are a length (proximal to distal direction) on the order of about 0.2 inches, a lateral width on the order of about 0.15 inches and a thickness on the order of 0.12 inches. FIG. 7 shows catheter holder 73 having opening 81 (e.g., circular opening) having a diameter suitable to accommodate catheter body 12 within the opening and a body of catheter holder 73. A representative diameter of opening 81 is on the order of about 0.06 inches. Catheter holder 73 is positioned in a housing of hub 51 such that opening is oriented distally. Catheter holder 73 also includes, in this embodiment, opening 82 on a side opposite opening 81 and in communication with opening 81 forming a lumen through catheter holder 73. Opening 82 has a dimension suitable to allow needle 46, needle 47, and inflation cannula 22 (an optionally support mandrel 17) to extend proximally from catheter holder 73. It is appreciated that a dimension (e.g., diameter) of opening 82 may be smaller than a dimension (e.g., diameter) of opening 81. Catheter holder 73 also includes, in this embodiment, opening 83 on a side adjacent to a side of opening 81. Opening 83 connects to opening 81 and may be used to introduce an adhesive to hold catheter body 12 within catheter holder 73. A representative diameter of opening 83 is on the order of about 0.06 inches. Although described as a component separate from the housing of hub 51, it is appreciated that can be formed as part of the housing (e.g., with mating portions formed in first housing half 71 and second housing half 72).

Referring to FIG. 6, once proximally past catheter holder 73, needle 46, needle 47, and inflation cannula 22 are positioned in different tracks (formed by mating cavities in the housing) that fan out as they extend proximally. Support mandrel 17 may terminate at catheter holder 73 with catheter body 12 or may extend proximally into the housing. Needle 46 and needle 47 are positioned on track 91 and track 92, respectively, that curve slightly to create the fanning within the housing. A portion (including the entire portion) of the track 91 and track 92 between catheter holder 73 and respective slider cavities 84 (described below) include track liners 74 within the tracks. Track liners 74 are, for example, a relatively low friction material such as TEFLON™ or high density polyethylene (HDPE) material that tends to facilitate needle movement, particularly within the curved track. In the embodiment described with reference to FIG. 1 and FIG. 6, inflation cannula 22 and optionally support mandrel 17 (if not terminated at catheter holder 73) extend proximally in a track within the housing of hub 51 between the track for needle 46 and needle 47.

Figure 8:
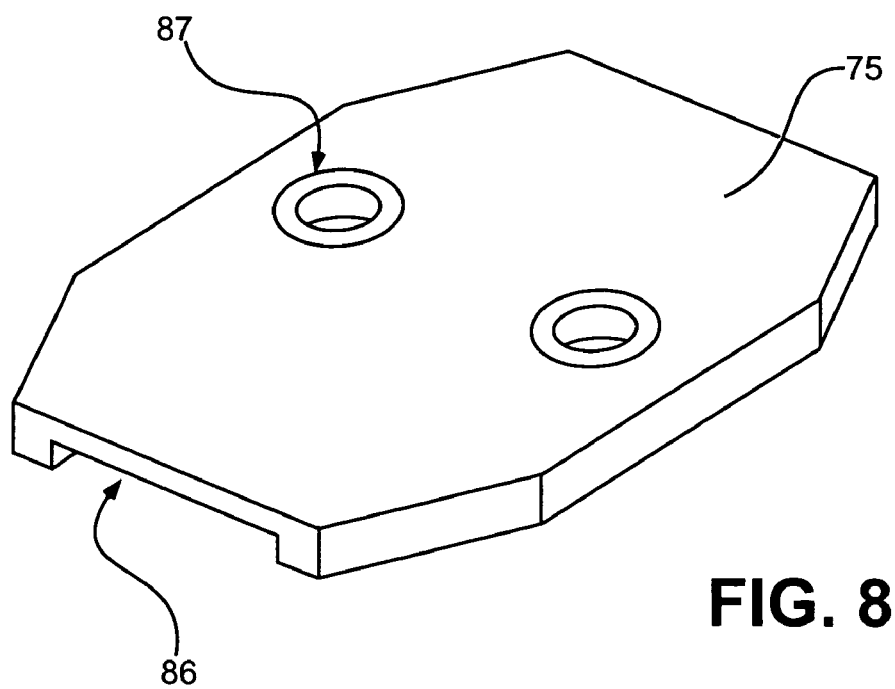
FIG. 8 shows a top and side perspective view of a cover plate in the housing of the hub of the catheter assembly of FIG. 1.

Referring to FIG. 1, proximal to catheter holder 73 of the housing of hub 51 is cover plate 75. Cover plate 75 has dimensions to fit within opening 85 of first housing half 71 (see FIG. 6). FIG. 8 shows a top side perspective view of an embodiment of cover plate 75. In this embodiment, cover plate 75 has a generally octagonal shape of a plastic or polymer material such a polycarbonate, a TEFLON™, or an ABS material. Cover plate 75 includes inferior disposed channel 86 extending in a proximal to distal direction. Channel 86 has a sufficient depth to accommodate a needle or inflation cannula therethrough. When placed in opening 85 of hub 51, cover plate 75 covers needle 46, needle 47, and inflation cannula 22 (and optionally support mandrel 17), with each of needle 46, needle 47, and inflation cannula 22 (and optionally support mandrel 17) disposed within channel 86. Cover plate 75 may be connected to hub 51 by screw fasteners or an adhesive. FIG. 8 shows openings 87 in a top side surface of cover plate 75 for fasteners. Although shown as a detachable component of the housing of hub 51, it is appreciated that cover plate 75 may be made as an integral part of the housing.

Extending proximally from cover plate 75 within the housing of hub 51, FIG. 1 and FIG. 6 illustrate that track 91 and track 92 for needle 46 and needle 47, respectively fan out (e.g., in a lateral direction). The fanning out is accomplished by curved tracks. FIG. 6 illustrates generally curved track 91 for needle 46 and curved track 92 for needle 47 in medial section 90 of the housing of hub 51. Inflation cannula track 93 is generally straight. Relative to inflation cannula track 93, track 91 and track 92 curve in opposite directions. Track 92, for example, modifies the direction of needle 47 from a first axial orientation to a different second axial orientation, the difference illustrated by angle, α, of, for example, 15° to 60°.

Referring to FIG. 6, proximal to medial section 90 of the housing of hub 51 and proximal to each of track 91 and track 92 is slider cavity 84. A representative length (distal to proximal direction) of slider cavity 84 is on the order of about 1.8 inches. Each slider cavity 84 has a lateral dimension (e.g., width) greater than respective ones of track 91 and track 92. Each slider cavity 84 has a lateral dimension suitable to accommodate a slider therein. Each slider cavity 84, in the embodiment shown in FIG. 6, has a generally rectangular shape. FIG. 6 shows slider 77 (in ghost lines) disposed within slider cavity 84 for needle 47. FIG. 1 shows sliders 77 connected to each of needle 46 and needle 47 within their respective slider cavities 84.

Figure 9:
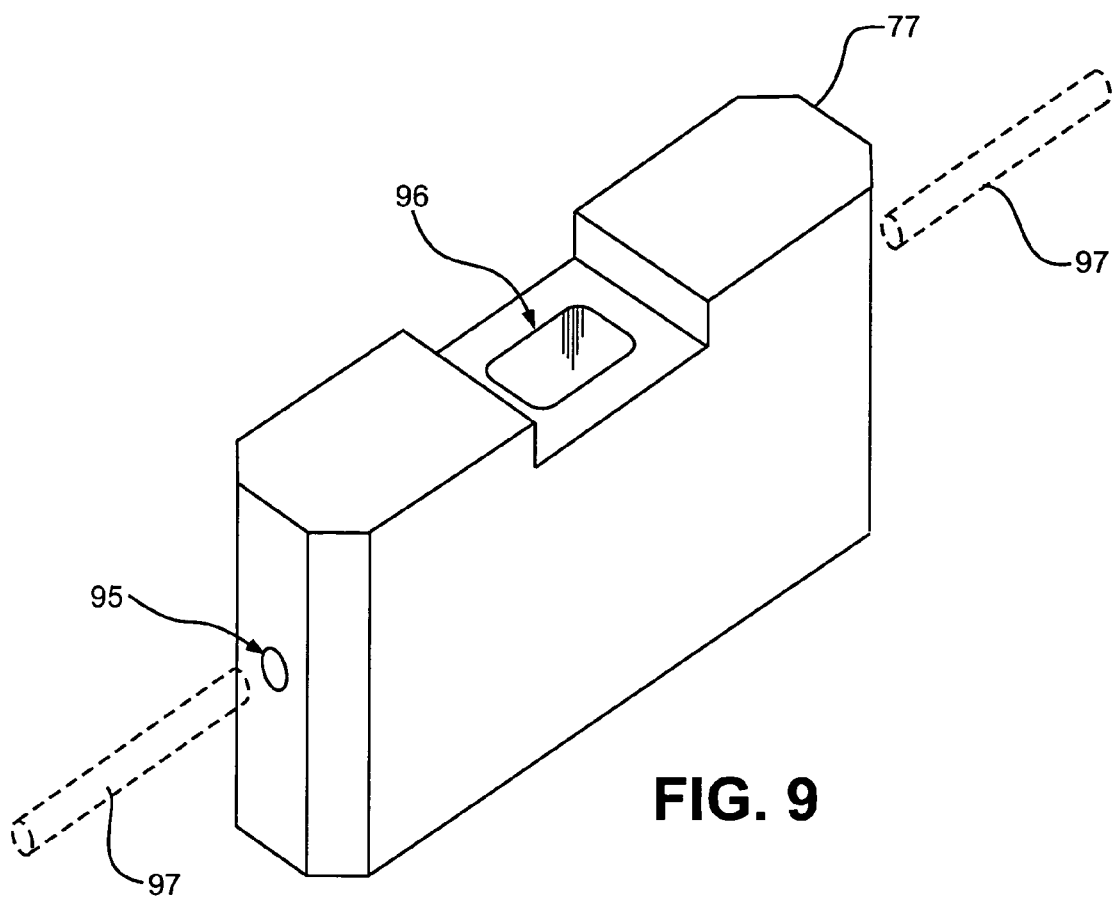
FIG. 9 shows a top and side perspective view of a slider in the housing of the hub of the catheter assembly of FIG. 1.

FIG. 9 shows a top side perspective view of an embodiment of slider 77. Slider 77 is, representatively, a plastic or polymer material such as a polycarbonate or an ABS material. Representatively, slider 77 of a polycarbonate material has a length (proximal to distal direction) on the order of about 0.4 inches, a lateral width on the order of about 0.22 inches, and a thickness on the order of about 0.078 inches. Slider 77 has opening 95 extending therethrough (in a proximal to distal direction) of a size to accommodate a needle (e.g., a diameter at least as large an outer diameter of needle 46 or needle 47, respectively, or an outer diameter of support tubes extending over a portion or portions of each needle). In one embodiment, each slider 77 is attached or fastened to a respective needle such as by an adhesive. As such, slider 77 acts as a protuberance on needle 47 increasing an outer dimension of needle 47. FIG. 9 shows slider 77 including side opening 96 or port (in a side notch) extending to opening 95 to allow an adhesive to be introduced once slider 77 is placed on a needle at a desired position. Each slider 77 along with each slider cavity 84 may serve at least two functions: to hold a needle in a desired rotation and minimize rotation; and to inhibit needle movement in both extension and retraction directions (e.g., to limit proximal and distal advancement). According to the first function, slider 77 serves as a proximal end orientation device. In a typical catheter assembly design such as catheter assembly 10, a needle associated with a catheter assembly is generally relatively long (e.g., 150 centimeters or more). It may be desirable to maintain an orientation of a needle so that a distal tip (typically a sharp tip) travels through the catheter assembly and enters a desired blood vessel or tissue at a prescribed orientation. Fixing the orientation at a distal portion or end of a catheter assembly does not necessarily guarantee the needle will have a desired orientation at a proximal end. Where the distal orientation is fixed, slider 77 serves to maintain a prescribed orientation at a proximal end and thus tends to reduce torsional stress on the needle or needle components (e.g., a distal needle orientation device).

Figure 10:
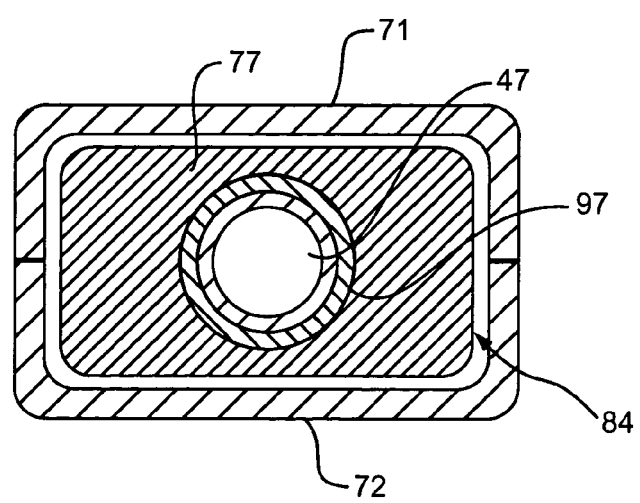
FIG. 10 shows a cross-sectional side view through line D-D' of FIG. 1.

In one embodiment, extending from opening 95 at a proximal and distal end of each slider 77 are, respectively, needle support tubes 97. FIG. 6 shows needle support tubes 97 (in ghost lines) extending from each end of slider 77. FIG. 10 shows a cross-section through line D-D' of FIG. 1. From this view, needle 47 is shown within and connected to support tube 97. FIG. 10 also shows slider 77 in the background (proximal) within slider cavity 84 created by first housing half 71 and second housing half 72 of hub 51. In one embodiment, support tubes 97 terminate within either proximal or distal side of opening 95 through slider 77 (see FIG. 6) prior to opening 96 at roughly, for example, a midpoint of the slider body. In this manner, sufficient volume or area remains to introduce adhesive and connect a needle (e.g., needle 47) to slider 77.

In one embodiment, needle support tubes 97 may support a needle in an area where the needle is not riding on a track, such as in slider cavity 84. Between slider 77 and the tracks (e.g., a distal side of slider 77), needle support tube 97 is, for example, a metal material including a shape memory alloy such as nitinol (NiTi). Support tube 97 may serve to inhibit kinking of a needle (e.g., needle 47) traveling in and out of the curved track (e.g., a portion of needle 47 traveling in and out of curved track 92 in medial section 90 of the housing of hub 51). Between slider 77 and an injection port for a needle, support tube 97 is, for example, a metal material such as stainless steel or a polymer material.

FIG. 1 shows a proximal end of needle 46 and needle 47 each connected (e.g., through an adhesive) to respective delivery port 98. In one embodiment, each delivery port 98 includes a luer fitting for conventional syringe attachment. Each delivery port 98 allows for the introduction of a treatment agent, including but not limited to a drug or cell (e.g., stem cell) therapy.

As noted above, inflation cannula 22 and optionally support mandrel 17 run in a middle track in the housing of hub 51. In one embodiment, support mandrel 17 terminates at the proximal end of catheter body 12 or under cover plate 75. Inflation cannula 22 terminates at the distal end of balloon inflation port 23. In one embodiment, inflation cannula 22 is connected to balloon inflation port 23 by an adhesive or a thermal bond. Within the housing of hub 51 at a proximal end is inflation cannula holder 99. Inflation cannula holder 99 is, representatively, a generally rectangular cube of a plastic or polymer material such as a polycarbonate, a TEFLON™ or an ABS material with dimensions suitable to be accommodated in the housing of hub 51. Inflation cannula holder 99 has a primary opening therethrough (proximal to distal opening) with a dimension large enough to accommodate an outer diameter of inflation cannula 22. A side adjacent to a proximal or distal end of inflation cannula holder 99 may have a secondary opening to the primary opening to allow an adhesive to be introduced to secure inflation cannula 22 to inflation cannula holder 99. Although described as a separate component, it is appreciated that inflation cannula holder 99 may be formed as an integral part of the housing of hub 51.

Figure 11:
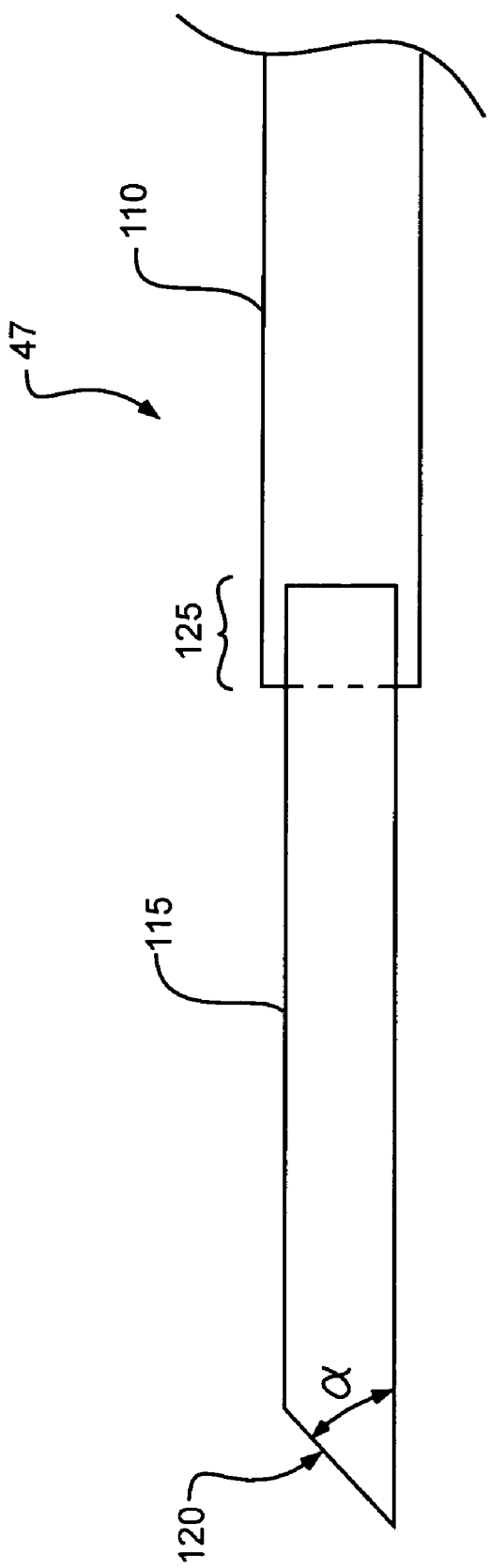
FIG. 11 shows a first embodiment of a needle body suitable for use in the catheter assembly of FIG. 1.

FIG. 11 shows an embodiment of a distal portion of needle 47. This distal portion of needle 47 itself includes proximal section 110 and distal section 115 each in the form of a cannula defining a single lumen therethrough. Proximal section 110, in this embodiment, is a material having sufficient column strength to make needle 47 pushable in the vasculature without buckling (e.g., sufficient column strength to be pushable by an operator outside the body of a subject). One suitable material is a stainless steel hypotube having a representative inner diameter of 0.009 inches and an outer diameter of 0.013 inches. Distal section 115 of needle 47 in this embodiment is a superelastic material with a relatively high degree of bending stress without permanent deformation of the material. A suitable material is a nickeltitanium alloy (e.g., nitinol) with a representative inner diameter of 0.004 inches and an outer diameter of 0.008 inches. In one embodiment, distal section 115 is inserted into proximal section 110 at union 125 a distance of approximately one centimeter (cm). A pressure-resistant connection is made through the use of an adhesive such as LOCTITE 3311 or welding or soldering the material together. In one embodiment, distal section 115 has a length ranging from one centimeter to about 10 centimeters. Proximal section 110 may have a length on the order of 150 cm. By combining a distal section with a relatively high degree of bending stress without permanent deformation of the material, needle 47 resists kinking that is believed to be a result of material for needle 47 being too stiff to easily track through the distal anatomy of, for example, the coronary arteries. The flexibility of distal section 115 also reduces the risk of premature needle tip puncture through a catheter side wall (e.g., delivery cannula 42), thus reducing the risk of unwanted or uncontrolled protrusions of a metal tip outside a cross-sectional profile of the catheter that could cause injury to a blood vessel during insertion or removal. In one embodiment, distal section 115 includes a beveled tip with a bevel angle, y, between 5° and 30°.

Needle 47 is slidably or movably disposed in a lumen of delivery cannula 42. Needle 47 includes, as described above with reference to FIG. 11, distal section 115 including beveled tip 120 having a dispensing port. The dispensing port is in fluid communication with a central lumen (not shown) of needle 47. In one embodiment, the lumen of needle 47 can be pre-filled with a measured amount of a treatment agent. The lumen of needle 47 connects the dispensing port with treatment agent substance delivery port 98 (see FIG. 1) that is configured to be connected to various substance dispensing means such as a syringe or fluid pump. Delivery port 98 allows a measured therapeutic substance to be dispensed as desired or on command.

Figure 12:
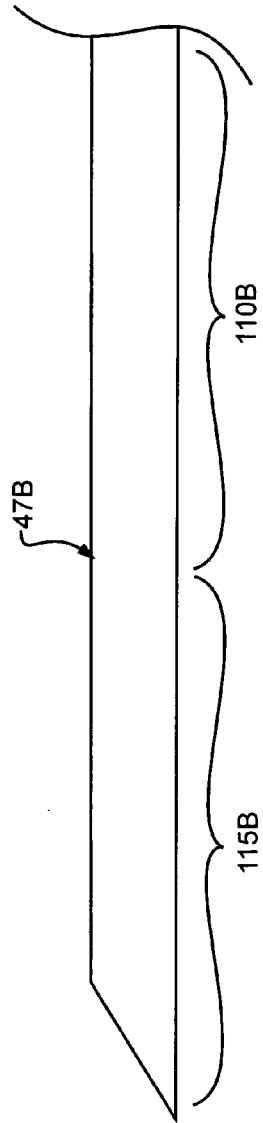
FIG. 12 shows a second embodiment of a needle body suitable for use in the catheter assembly of FIG. 1.

In addition to the embodiment described in FIG. 11, needle 47 can be constructed in several different ways. FIGS. 12-15 illustrate some exemplary embodiments of suitable needle constructions. FIG. 12 illustrates that in one embodiment, needle 47B has a constant needle diameter throughout proximal section 110B and distal section 115B of the needle. In this embodiment, the constant diameter needle can be manufactured of a single material or welding two similar diameter components together.

Figure 13:
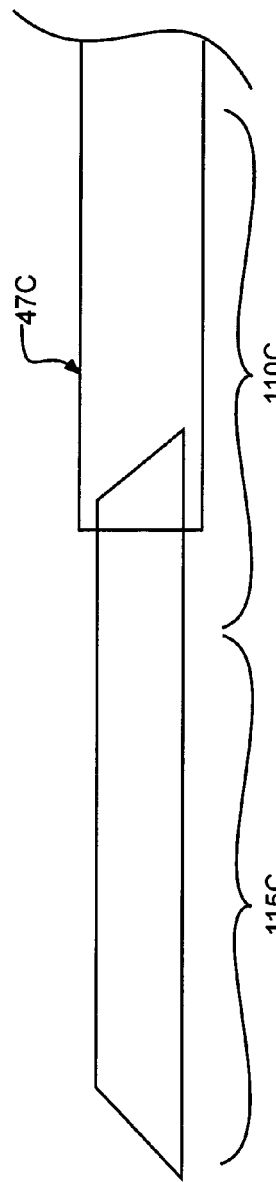
FIG. 13 shows a third embodiment of a needle body suitable for use in the catheter assembly of FIG. 1.
Figure 14:
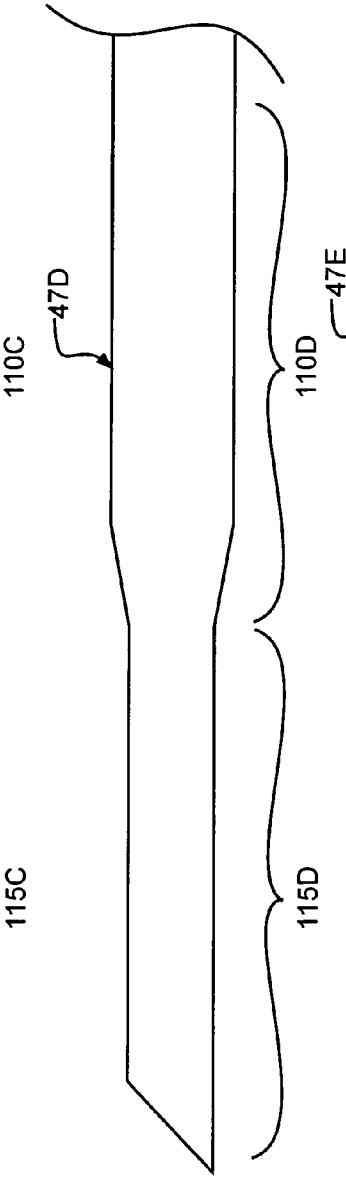
FIG. 14 shows a fourth embodiment of a needle body suitable for use in the catheter assembly of FIG. 1.
Figure 15:
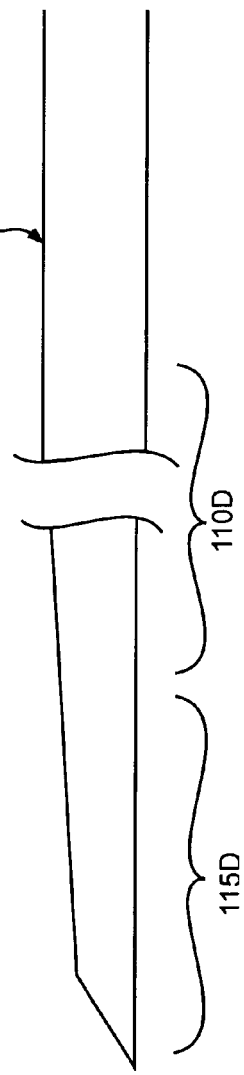
FIG. 15 shows a fifth embodiment of a needle body suitable for use in the catheter assembly of FIG. 1.

FIG. 13 illustrates a needle configuration similar configuration to that of FIG. 12. In this embodiment, distal section 115C of the needle 47C is ground (or shaped) to a beveled end to reduce the abruptness of a transition with proximal section 110C and increase a transition point inner diameter (e.g., round vs. oval opening). FIG. 13 shows distal section 115C fitting within proximal section 110C. In one embodiment, an outside diameter and an inside diameter of distal section 115C is less than an outside diameter and an inside diameter of proximal section 110C. In this manner, distal section 115C steps down from proximal section 110C. FIG. 14 illustrates an embodiment where needle 47D has a tapered transition, for example, tapered distal section 115D relative to proximal section 110D. FIG. 15 illustrates an embodiment where needle 47E is a one or two piece needle wherein the needle is tapered at proximal section 110D of the needle (e.g., reduced outside and inside diameter compared to the remainder of the needle) and a minimum profile maintained through a majority of the length of the needle including distal section 115D.

FIG. 16 shows delivery cannula 42 of catheter assembly 10 (see FIG. 1) prior to inflation or dilation of balloon 20. A sheath ring is omitted in this FIG. In this view, delivery cannula 42 is connected to one surface (a superior surface as viewed) to balloon 20 (shown in ghost lines). In this embodiment, delivery cannula 42 has a linear profile (e.g., lying in a longitudinal plane through an axis along its length). Delivery cannula 42 includes a lumen therethrough that accommodates needle 47. Delivery cannula 42 also includes distal section 130 and proximal section 140. Distal section 130 includes opening 135 for needle 47 to be advanced therethrough to, for example, a region of interest or treatment site such as a tissue site. Distal section 130 of delivery cannula 42 may be connected to (adhered to) proximal taper wall 36 of balloon 20 by, for example, an adhesive (e.g., a cyanoacrylate adhesive).

FIG. 16 also shows delivery cannula 42 including plication region 150 differentiating distal section 130 from proximal section 140 of delivery cannula 42. In one embodiment, delivery cannula 42 is capable of plicating or bending (or generally rotating) about a pivot point at plication region 150 in response to the inflation (dilation) of balloon 20. In one embodiment, distal section 130 can move from a substantially longitudinal position to a substantially perpendicular position. Thus, an angle can vary between 0° and 90° (see FIG. 1). In one example, after inflation of balloon 20, angle can range from between about 30° and 60°, for example, 45°.

The embodiment of delivery cannula 42 shown in FIG. 16 also includes deflector 160 disposed along an interior wall (as viewed) of delivery cannula 42. In one embodiment, deflector 160 can be any device that will provide a shield to protect a wall of delivery cannula 42 while being small enough such that deflector 160 does not impact the track of catheter assembly 10 (see FIG. 1) in any significant manner. In one embodiment, deflector 160 can be a ribbon of thin, generally flexible and generally resilient material such that deflector 160 can move and bend as distal section 130 and proximal section 140 of delivery cannula 42 bend and move relative to each other. Deflector 160 also provides a surface upon which needle 47 can be made to track through plication region 150. In one embodiment, deflector 160 is a size such that it fits into and along an inner wall of delivery cannula 42 without occluding or interfering with the ability of needle 47 to translate through plication region 150. For example, deflector 160 can have a thickness of between about 0.0005 inches and about 0.003 inches. A width of deflector 160 may, in one embodiment, be between about 0.005 inches and 0.015 inches. A length of deflector 160, in one embodiment, may extend from distal section 130 of delivery cannula 42 to a point along proximal section 140 of delivery cannula 42. A suitable length is between about one centimeter (cm) and about 10 cm. Deflector 160 can be made of any suitable material that allows deflector 160 to function, such as stainless steal, platinum, aluminum, and alloy materials with similar material properties. In one embodiment, deflector 160 can be made from a super elastic alloy, such as nitinol.

In one embodiment, deflector 160 has distal section 161, medial section 162 and proximal section 163. In one embodiment, distal section 161 can be supported by delivery cannula 42 by bonding distal section 161 to the inner wall of distal section 161 of delivery cannula 42. In one embodiment, the bonding is done by applying an adhesive on the back surface of distal section 161 of deflector 160 and adhering it to the inner wall of distal section 130 of delivery cannula 42. Alternatively, distal section 161 of deflector 160 may be heat fused onto the polymer of the wall of distal section 130 of delivery cannula 42. During a heat fuse process, a mandrel may be inserted into a lumen of delivery cannula 42 to keep the lumen open and a removable shrink tube is placed over the outside diameter of the cannula at least over distal section 130 to maintain an outer diameter when the polymer is softened by heat. Delivery cannula 42 is then heated to fuse deflector 160 to the cannula. After the heat fusion, the mandrel and shrink wrap are removed.

FIG. 16 shows an embodiment in which a portion of proximal section 163 of deflector 160 is outside of a lumen of delivery cannula 42 such that a wall of the cannula separates the needle from the deflector. One reason for positioning proximal section 163 of deflector 160 outside of the lumen is to avoid dislodging (e.g., "peeling up") of deflector 160 due to the movement of needle 47. In one embodiment, proximal section 163 exits out of delivery cannula 42 and is adhered to an outside wall of delivery cannula 42 using, for example, an adhesive, such as glue or the like. In the embodiment shown in FIG. 16, medial section 162 of deflector 160 is disposed on an inner wall of delivery cannula 42, such that as delivery distal section 130 bents or rotates at plication region 150 relative to proximal section 140, deflector 160 is positioned over an outside of the curvature of plication region 150 and bends along medial section 162.

FIG. 17 shows delivery cannula 42 in a deployed configuration. According to this illustration, balloon 20 has been inflated (dilated) and distal section 130 of delivery cannula 42 is plicated, deflected, rotated or bent at plication region 150 at an angle. Distal section 130 is connected to proximal taper wall 36 of balloon 20 and adopts a shape in response to the shape of proximal taper wall 36 of balloon 20. Proximal section 140 remains in a generally longitudinal configuration corresponding with the longitudinal configuration of catheter assembly 10 proximal to the balloon (see FIG. 1).

FIG. 17 shows additional components in a lumen of delivery cannula 42. Specifically, delivery cannula 42 includes needle 47, needle sheath stop 170, needle stop 180, and pullback stop 190. In one embodiment, needle sheath stop 170, needle stop 180, and pullback stop 190 are included to control the advancement of needle 47 (a distal control relative to the proximal control described above with reference to FIGS. 1, 6 and 9-10 and the accompanying text describing sliders 77 and slider cavities 84). In one embodiment, needle sheath stop 170 limits the advancement of needle 47 (e.g., the advancement beyond opening 135 into tissue such as a blood vessel wall or myocardial tissue). Needle sheath stop 170 is connected to the interior wall of delivery cannula 42 by, for example, an adhesive or thermal bonding. Needle sheath stop 170 is in one perspective a protuberance (e.g., a sleeve protuberance) on an inner wall of delivery cannula 42. As a sleeve protuberance, needle sheath stop representatively has an inner diameter of 0.0093 inches and an outer diameter of 0.0123 inches. In one embodiment, needle sheath stop 170 is positioned at a point proximal to plication region 150 along proximal section 140 of a distal portion of delivery cannula 42. A suitable material for needle sheath stop 170 is a polyimide material in one embodiment formed into a sleeve having an opening therethrough to accommodate needle 47 and sufficient structural integrity to block the advancement of needle 47 beyond a contact point at which needle sheath stop 170 is contacted.

Delivery cannula 42 also includes needle stop 180. In one embodiment, needle stop 180 has a size sufficient to be accommodated in a lumen of delivery cannula 42 and is connected to needle 47. From one perspective, needle stop is a protuberance on an exterior surface of needle 47. Needle stop 180 as a sleeve (e.g., a sleeve protuberance) has a lumen therethrough of a diameter slightly greater than needle 47 so that it may be affixed to needle 47. Suitable material for needle stop 180 where needle 47 is a metal material include a similar or compatible metal material. Needle stop 180 may be attached to needle 47 by an adhesive, welding, soldering, or pressing needle stop 180 against needle 47. An outer diameter or dimension of needle stop 180 has a diameter slightly less, in one embodiment, than the diameter of a lumen of delivery cannula 42. Needle stop 180 and needle 47 are freely movable in a lumen of delivery cannula 42 but needle stop 180 has an outer diameter that is greater than an inner diameter of needle sheath stop 170 so that needle sheath stop 170 acts as a distal travel stop for needle 47. Representative dimensions for needle stop 180 as a sleeve is a length on the order of 0.050 inches, an outer diameter on the order of 0.014 inches, an inner diameter of 0.009 inches and a base (a D-shaped base) on the order of 0.016 inches. In one embodiment, needle stop 180 is a material suitable for connecting to needle 47.

Pullback stop 190 is also optionally accommodated in a lumen of delivery cannula 42. In one embodiment, pullback stop 190 is connected to an inner wall of delivery cannula 42. From one perspective, pullback stop 190 is a protuberance on an interior surface of delivery cannula 42. As a sleeve (e.g., a sleeve protuberance), pullback stop 190 allows a portion of needle 47 (that portion proximal to needle stop 180) to be advanced through a lumen through pullback stop 190. Thus, pullback stop 190 resides in delivery cannula 42 at a position proximal to needle stop 180. Needle stop 180 resides in delivery cannula 42 at a position proximal to needle sheath stop 170. In one embodiment, pullback stop 190 inhibits needle 47 from retracting proximally. One reason to constrain the proximal movement of needle 47 is to minimize puncturing of delivery cannula 42, thus inhibiting potential damage during application. In one embodiment, pullback stop 190 is made of a flexible metallic or non-metallic material or a combination of both. A polyimide tubing having exterior dimensions slightly less than the interior dimension of delivery cannula 42 and a lumen having a dimension suitable to accommodate needle 47 is appropriate.

FIGS. 18-22 show various cross-sections through different points along delivery cannula 42 of FIG. 17. FIG. 18 shows a cross-section of delivery cannula through line A-A'. In this embodiment, a lumen delivery cannula 42 is shown as generally D-shaped resulting from deflector 160 as a flat ribbon connected to an interior wall of delivery cannula 42. Needle 47, at this point, is generally circular and disposed in a lumen of delivery cannula 42. FIG. 19 shows a cross-section of delivery cannula through line B-B'. A lumen of delivery cannula 42 is D-shaped or non-circular due to deflector 160. Needle sheath stop 170 is connected to an interior wall of delivery cannula 42 and generally conforms to an inner diameter of delivery cannula 42. Needle sheath stop 170 is shown as a sleeve connected to an inner wall of delivery cannula 42 and having a generally circular lumen therethrough. The lumen of needle sheath stop 170 may alternatively have a D-shape or non-circular shape corresponding to the lumen of delivery cannula 42. Needle 47, in one embodiment, has a similar circular cross-section at this point so that needle 47 may be advanced or retracted through needle sheath stop 170. FIG. 19 shows needle sheath stop 170 having a lumen therethrough with an interior dimension suitable to accommodate the proximal or distal advancement of needle 47.

FIG. 20 shows a cross-section of delivery cannula 42 through line C-C'. In this embodiment, delivery cannula 42 has a lumen, at this point, with a D-shape or non-circular shape due to the presence of deflector 160. Disposed within delivery cannula 42 at this point is needle stop 180 also having a D-shape conforming to the lumen of delivery cannula 42. Needle 47 also has a D-shape or may have a circular shape. In this view, needle 47 is shown connected to needle stop 180. The outer dimension of needle stop 180, as a sleeve (e.g., a sleeve protuberance), is less than an inner dimension of delivery cannula 42 so that needle stop 180 may be proximally or distally advanced through delivery cannula 42. Needle stop 180 establishes an orientation of needle 47 within delivery cannula 42. In one embodiment, the established orientation orients a tip of needle 47 within a portion of delivery cannula 42 that includes deflector 160 so that the tip of needle 47 may contact deflector 160 and reduce the possibility that the tip of needle 47 will puncture the upper interior (superior) surface of delivery cannula 42. In another embodiment, one or both of needle 47 and needle stop 180 have generally circular profiles and the presence of deflector 160 modifies a profile of one or both of needle 47 and needle stop 180 at line C-C' to establish an orientation of needle 47 within delivery cannula 42 (e.g., deflector 160 modifies one or both needle 47 and needle stop 180 to a D-shaped cross-section).

FIG. 21 shows a cross-section through line D-D' of FIG. 17. In this view, a lumen of delivery cannula 42 has a D-shape or non-circular shape due to the presence of deflector 160. Connected to the inner walls of delivery cannula 42 is pullback stop 190. Pullback stop 190, in this embodiment, is a sleeve that generally conforms to the D-shape with a lumen therethrough. An inner dimension of pullback stop 190 is defined such that needle 47 may be advanced, proximally or distally, therethrough. In this embodiment, needle 47 has a circular shape.

FIG. 22 shows a cross-section through line E-E' of FIG. 17. In this embodiment, a lumen of delivery cannula 42 has a D-shape or non-circular shape due to the presence of deflector 160. Pullback stop 190 is disposed in a lumen of delivery cannula 42 and connected to the inner wall of delivery cannula 42. Pullback stop 190, in this embodiment, is a sleeve (e.g., a sleeve protuberance) that conforms to the shape of a lumen of delivery cannula 42. FIG. 22 also shows needle 47 disposed in a lumen of pullback stop 190 such that needle 47 may be advanced, proximally or distally, therein.

In the above embodiment, a technique for orienting a position of needle 47 is described. Specifically, the D-shaped cross-section shown in FIG. 20 (needle stop 180) orients needle 47 in a particular way as it is advanced proximally or distally through delivery cannula 42. In this manner, as needle 47 is advanced beyond opening 135 adjacent or into tissue (see FIG. 17), needle 47 will be in a desired orientation (e.g. the tip of needle 47 adjacent deflector 160). The embodiment takes advantage of the presence of deflector 160 in a lumen of delivery cannula 42. Deflector 160 modifies the shape of the lumen to, in one embodiment, a D-shape cross-section. Needle stop 180 is configured with an exterior dimension (diameter) smaller than an interior diameter of the lumen of delivery cannula 42 but large enough so that it must conform to the shape of the lumen to be movable within the lumen. As an alternative to the above technique for orienting a position of a needle, in another embodiment, a cross-section of a portion of delivery cannula 42 may be modified to define a lumen of a particular shape (such as a D-shape). Alternatively, needle 47 may have a non-circular shape (e.g., rectangular, D-shaped, etc.), at least at a distal end, that limits possible orientations within delivery cannula 42.

In one embodiment, needle stop 180 is positioned between needle sheath stop 170 and pullback stop 190 so that needle 47 may be advanced distally a distance L1. Referring again to FIG. 17, needle 47 is positioned within needle cannula 42 so that a distal end of needle 47 extends through needle sheath stop 170 a protruding distance L2. Thus, when needle 47 is distally advanced, needle stop 180 may travel a length L1 before it contacts a proximal side of needle sheath stop 170. Needle sheath stop 170, by having a dimension that will reduce an inner dimension (diameter) of a lumen of delivery cannula 42 to a lumen smaller than an outer cross-sectional dimension of needle stop 180, will limit the advancement of needle stop 180, and thus limit the distal advancement of needle 47. Optionally, a distal side of needle stop 180 may be grounded while a proximal side of needle sheath stop 170 is connected to a voltage source, for example, a five volt direct current battery. In this embodiment, contact between needle stop 180 and needle sheath stop 170 completes an electrical circuit, that may include an alarm, such as a beep or a flashing light-emitting diode to indicate to an operator that a distal advancement lumen has been reached. A similar electrical configuration may be used to indicate contact between a proximal side of needle stop 180 and a distal side of pullback stop 190.

Figure 23:
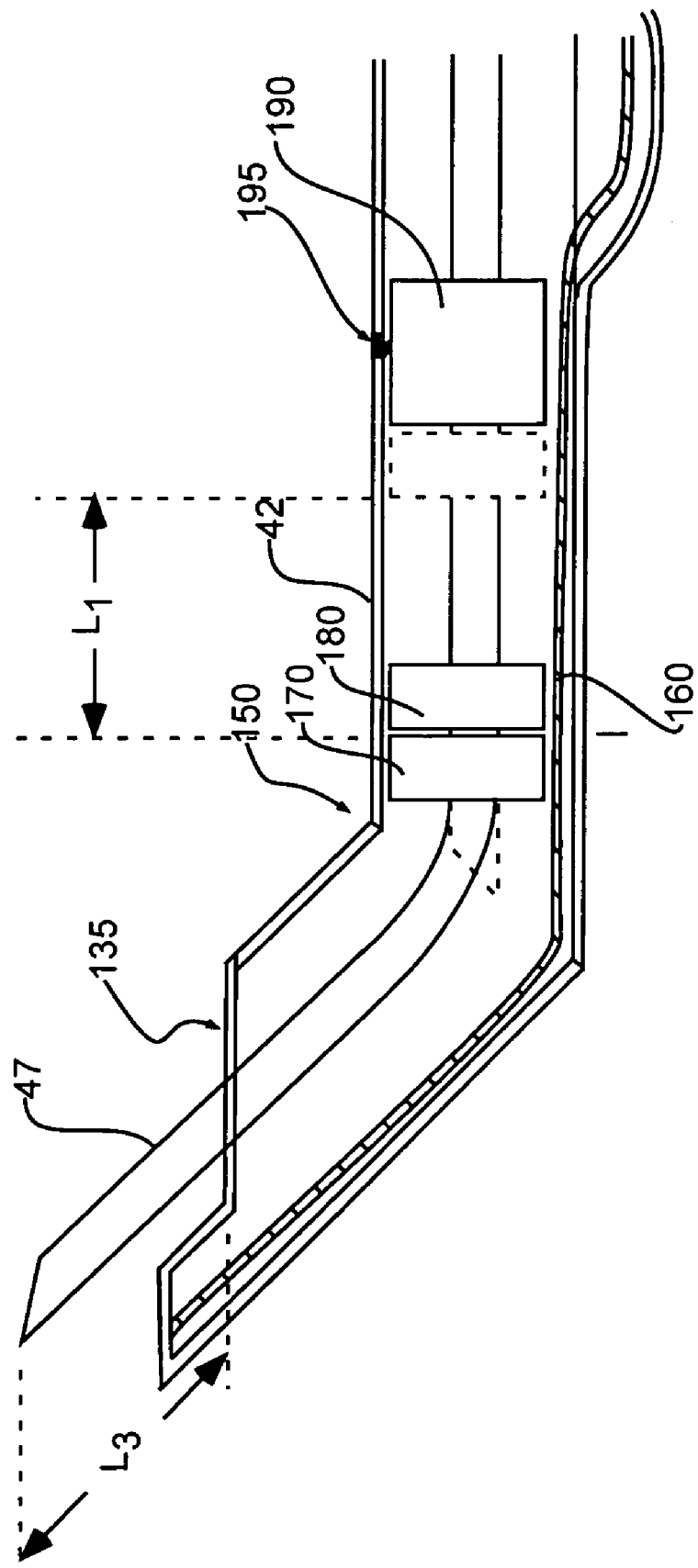
FIG. 23 shows the portion of the delivery cannula of FIG. 17 with a needle in a deployed state.

FIG. 23 shows needle stop 180 distally advanced a distance L1 so that it contacts a proximal side of needle sheath stop 170. In one embodiment, the distance L1 combined with the protruding distance L2 is selected so that needle 47 will extend a distance, L3, beyond opening 135 of delivery cannula 42, for example adjacent a blood vessel, into a blood vessel, or beyond a blood vessel (e.g., into myocardial tissue). A representative extension distance of needle 47 beyond opening 135 in delivery cannula 42 is on the order of 0.65 mm to 0.85 to locate the needle in a periadventitial or adventitial tissue of a blood vessel and a larger distance to locate needle 47 in muscle tissue.

In the embodiment described, needle sheath stop 170 is positioned at a point proximal to plication region 150. An advancement distance, L1, may be selected by predicting an advancement distance and soldering needle stop 180 to needle 47 at a point consistent with the predicted distance. Needle 47 may then be advanced until needle stop contacts needle sheath stop 170. The predicted distance may then be measured. If the predicted advancement distance provides an acceptable extension distance of needle 47, needle stop 180 is properly positioned on needle 47. If the extension distance is too short or too long, needle stop 180 may be repositioned by, for example, heating the solder joint to loosen the connection between needle stop 180 and needle 47 and needle stop 180 is repositioned on needle 47 and re-soldered.

Once needle stop 180 is positioned as desired on needle 47, pullback stop 190 may be placed. One way to place pullback stop 190 is to remove needle 47 from catheter assembly 10 and place pullback stop 190 on needle 47 proximal to needle stop 180. Needle 47 including pullback stop 190 may then be advanced distally through catheter assembly 10 including into delivery cannula 42. A mandrel may be used to advance pullback stop 190. Pullback stop 190 is placed at a desired position within delivery cannula 42. Hole 195 (see FIG. 17) may be bored through delivery cannula 42 at a position coinciding with a position within a lumen of delivery cannula 42 of pullback stop 190. An adhesive may be introduced into hole 195 to fix pullback stop 190 at the desired position (connecting pullback stop 190 to delivery cannula 42).

It is appreciated that the embodiment described with reference to FIGS. 17-23 described needle sheath stop 170, needle stop 180, and pullback stop 190 each as sleeves around an inner wall of delivery cannula 42 or needle 47. It is appreciated that one or more stops may have alternative configurations such as partial sleeves or bump protuberances. The embodiment described also included a pullback stop. It is appreciated that once a pullback stop is positioned in a delivery cannula, a needle in the same cannula will not be able to removed. Therefore, in situations where it may be desirable to remove a needle during a procedure, a pullback stop may be omitted.

Figure 24:
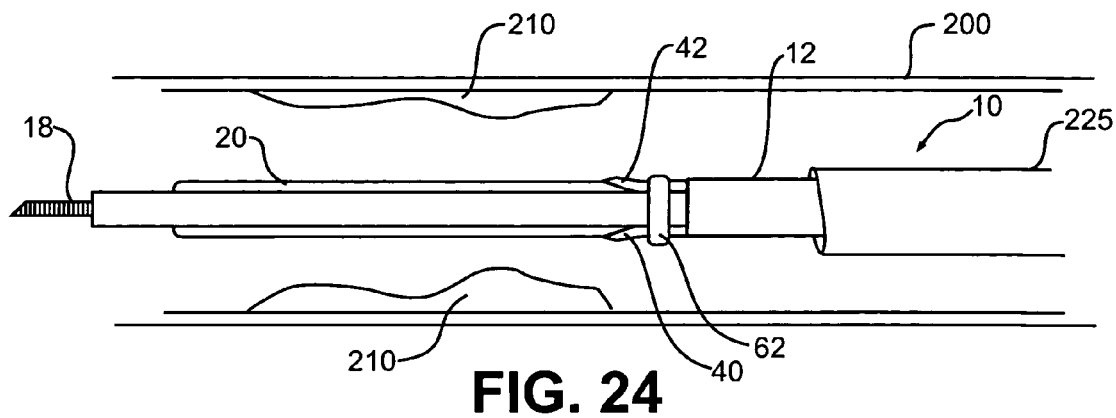
FIG. 24 shows a simplified cross-sectional side view of a portion of an artery with an embodiment of a catheter assembly of FIG. 1 disposed therein with a balloon of the catheter assembly in a deflated state.
Figure 25:
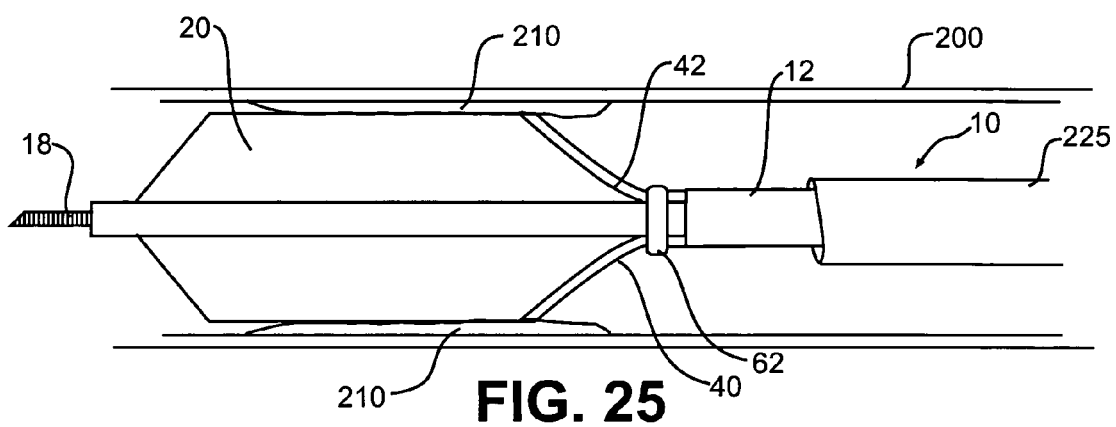
FIG. 25 shows the portion of the artery of FIG. 24 with a balloon of the catheter assembly in an inflated state and needles in respective delivery cannulas in a retracted state.
Figure 26:
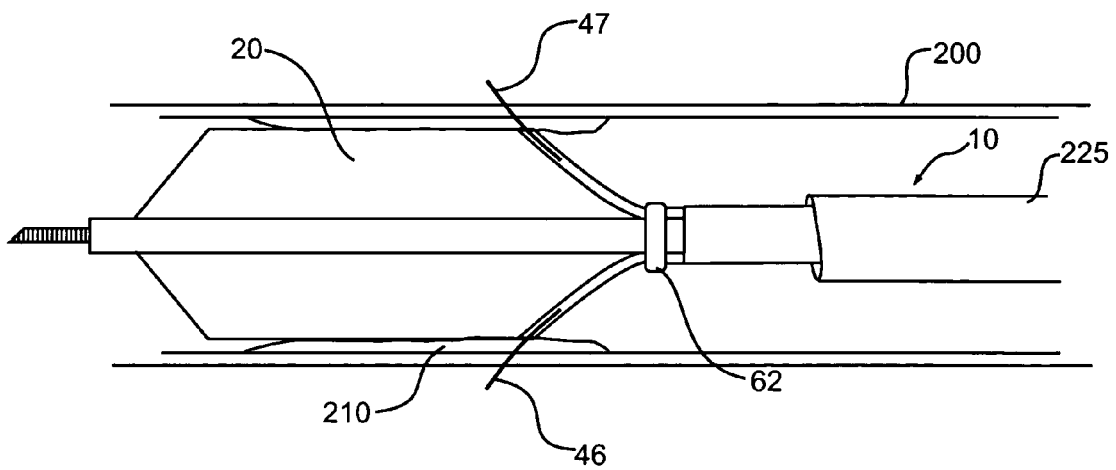
FIG. 26 shows the portion of the artery of FIG. 24 with a balloon of a catheter assembly in an inflated state and needles in respective delivery cannulas in a deployed (advanced) state.

As previously mentioned, transluminal angioplasty is a technique that is frequently used to enlarge a blood vessel, such as a coronary artery, that has become occluded by the build up of plaque, or to prevent or treat arterial restenosis and possibly to promote an angiogenic response in an ischemic heart. FIGS. 24-26 illustrate the use of catheter assembly 10 to reopen a narrowed lumen of a coronary artery.

FIG. 24 shows coronary artery 200 having stenotic region 210 of occluding materials, such as plaque or other material (e.g., fatty deposits) occluding a portion of a lumen of artery 200. In one procedure, guidewire 18 of catheter assembly 10 may be introduced into the arterial system of a patient until a distal end of guidewire 18 reaches the narrowed lumen of artery 200, and possibly extend beyond the narrowed lumen of artery 200 (beyond occluding material 220). Catheter assembly 10 may then be mounted on a proximal end of guidewire 18 and translated distally along guidewire 18 until catheter assembly 10 is positioned as desired in a narrowed lumen. It is appreciated that various imaging techniques may be used to position catheter assembly 10 as desired. Typical imaging techniques include, but are not limited to, fluoroscopic techniques, ultrasonic techniques, (intravascular ultrasound (IVUS)), nuclear magnetic resonance imaging (MRI) and optical coherent tomography (OCT). Various techniques may require markers on components of catheter assembly 10 or guidewire 18, for example, including radiopaque or MRI compatible or incompatible markers. Alternatively, in the case of OCT, for example, a light source may be included, for example, in a separate lumen in catheter assembly 10, to position catheter assembly 10 at stenotic region 210.

FIG. 24 shows catheter assembly 10 having balloon 20 in a deflated state and delivery cannulas 40 and 42 with, for example, needles 46 and 47, respectively, disposed therein, lying in a substantially longitudinal arrangement with balloon 20 and the remainder of catheter assembly 10. Catheter assembly 10 is advanced along guidewire 18 to a desired position in artery 200, so that balloon 20 overlays at least a portion of stenotic region 210. In one embodiment, catheter assembly 10 may include sheath 225 of a cannula having a lumen therethrough enclosing the various described components of catheter assembly 10 at a distal end. Once catheter assembly 10 is deployed at a region of interest (e.g., stenotic region 210), sheath 225 may be retracted to expose balloon 20 and delivery cannula 40 and delivery cannula 42.

Referring to FIG. 25, once catheter assembly 10 is positioned with balloon 20 overlaying at least a portion of stenotic region 210, balloon 20 is inflated (dilated) by delivering a liquid to balloon 20 through inflation cannula 22 (see FIG. 1). Inflating balloon 20 causes balloon 20 to engage and contact the material or tissue built up on the interior wall of artery 200 at the stenotic region. The inflation of balloon 20 also causes delivery cannula 40 and delivery cannula 42 to adopt a shape at the distal end corresponding to a proximal taper wall of balloon 20. In one embodiment, a distal end of each of delivery cannula 40 and delivery cannula 42 may contact material within stenotic region 210 or an inner wall of artery 200. In one embodiment, sheath ring 62 is proximal to balloon 20 and serves to prevent delivery cannula 40 or delivery cannula 42 from separating from balloon 20.

FIG. 26 shows catheter assembly 10 after the deployment of needle 46 and needle 47. To deploy needle 46 and/or needle 47, each respective needle may be pushed distally for example to pierce the wall of artery 200 (needle 46) or extend beyond a wall of artery 200 (needle 47). The distal advancement of needle 46 and needle 47 may be made at hub 57 and hub 58, respectively, exterior to a subject. Referring again to FIG. 16 and FIG. 23, it will be appreciated that needle 47 (and needle 46) must be able to track around bend or plication region 150 so as to travel through delivery cannula 42 (and delivery cannula 40) to extend beyond an opening in the cannula. As illustrated in FIG. 16, FIG. 17, and FIG. 23, deflector 160 is positioned across plication region 150 on the outside of the bend curvature (as viewed). A tip of needle 47 (and a tip of needle 46) is oriented to contact deflector 160. As the needle is distally urged through plication region 150, deflector 160 helps to "bounce" the needle tip off the delivery cannula wall, allowing the needle to travel through without puncturing the delivery cannula wall.

Once needle 46 and/or needle 47 have been deployed, a treatment agent may be injected through needle 46 and/or needle 47 into the wall of artery 200 (needle 46) or beyond the wall of artery 200 (needle 47). Once a treatment agent has been injected, needle 46 and/or needle 47 may be retracted into delivery cannula 40 and/or delivery cannula 42, respectively. Balloon 20 may then be deflated and catheter assembly 10 withdrawn from artery 200, perhaps for tracking to another treatment location.

In FIGS. 24-26, an embodiment has been described for use during or after an angioplasty procedure. It is appreciated that catheter assembly 10 may be used to administer a treatment agent independent of any other procedure. Further, during some procedures it may be necessary or desirable to administer more than one type of treatment agent to the same tissues or to administer same treatment agent to more than one location in the tissue. Accordingly, a catheter assembly may be provided which includes a number of delivery assemblies including, for example, more than one delivery cannula 40 and/or delivery cannula 42 and more than one needle. Further, it is appreciated that catheter assembly 10 may be used in various applications. For example, by adjusting the puncture depth of needle 46 and/or needle 47, a treatment agent may be administered to either the tissue of an artery wall or myocardial tissue.

Suitable treatment agents that may be delivered through needle 46 and/or needle 47 during a procedure can include, but are not limited to, antineoplastic, antiinflammatory, antiplatelet, anticoagulant, antifibrin, antithrombin, antimitotic, antiproliferative, antibiotic, antioxidant antiallergic substances and combinations thereof. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocore). Examples of suitable antimitotic agents include mathotrexate, azathioprine, vincristine, vinblastine, fluorouracil, adriamycin, mutamycin and actinomycin D. Examples of suitable cytostatic or antiproliferative agents include angiopeptin (a somatostatin analogue from Ibsen), angiotensin converting enzyme inhibitors such as Captopril® (available from Hofman-LaRoche), or Lisinopril® (available from Merck); calcium channel blockers (such as Nifedipine), colchicine, fibroblast growth factor (FGF) antagonists, fish oil (omega 3-fatty acid), histamine antagonist, Lovastatin® (an inhibitor of HMG-CoA reductase, a cholesterol lowering drug from Merck), monoclonal antibodies (such as Platelet-derived Growth Factor (PDGF) receptors), nitroprusside, phosphodiesterase inhibitors, prostaglandin inhibitor (available from Glazo), Seramin (a PDGF antagonist), serotonin blockers, steroids, thioprotease inhibitors, triazolopyrimidine (a PDGF antagonist), and nitric oxide. An example of an antiallergic agent includes Permirolast potassium. Other therapeutic substances or agents which may be appropriate include alpha-interferon, genetically engineered epithelial cells, dexamethasone, and growth factors such as FGF, PDGF, Vascular Entothelial Growth Factor (VEGF), and stem cells. While the foregoing therapeutic substances or agents are well known for their preventative and treatment properties, the substances or agents are provided by way of example and are not meant to be limiting. Other therapeutic substances which are currently available or that may be developed are equally applicable.

Figure 27:
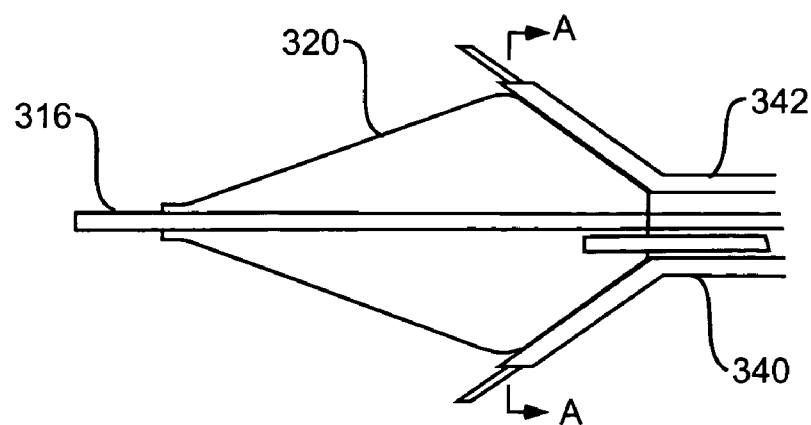
FIG. 27 shows a simplified sectional side view of a distal portion of a assembly including another embodiment of a balloon.

In the embodiment described with reference to FIGS. 1-26, catheter assembly 10 describes balloon 20 having a generally cylindrical working length. To deliver a treatment agent through a catheter assembly such as catheter assembly 10, it is appreciated that the working length of the balloon need not contact a blood vessel or approximate an interior diameter of a blood vessel. FIG. 27 illustrates another embodiment of a suitable balloon for use in a catheter assembly such as catheter assembly 10. Representatively, balloon 320 has a tapered profile, tapered along a working length from a proximal to distal end. At a proximal end, a diameter of balloon 320 has a suitable diameter such that balloon 320 may contact a blood vessel at a region of interest. In this manner, delivery cannulas 340 and 342 may deliver a needle and treatment agent to a region of interest. Beyond a proximal end of the working length of balloon 320, the balloon tapers to a distal end or portion having a dimension (diameter) to accommodate guidewire cannula 316. A configuration such as shown in FIG. 27 minimizes the possible contact between balloon 320 and a blood vessel wall, thus minimizing any possible undesired injury to a blood vessel wall, such as damage to an endothelial cell layer. Having a reduced working length also reduces the balloon inflation volume and therefore, tends to reduce deflation time. Reduced deflation time allows for a reduction in the size (diameter) of an inflation cannula (e.g., inflation cannula 22) and, in turn, tends to reduce a catheter shaft profile.

Figure 28:
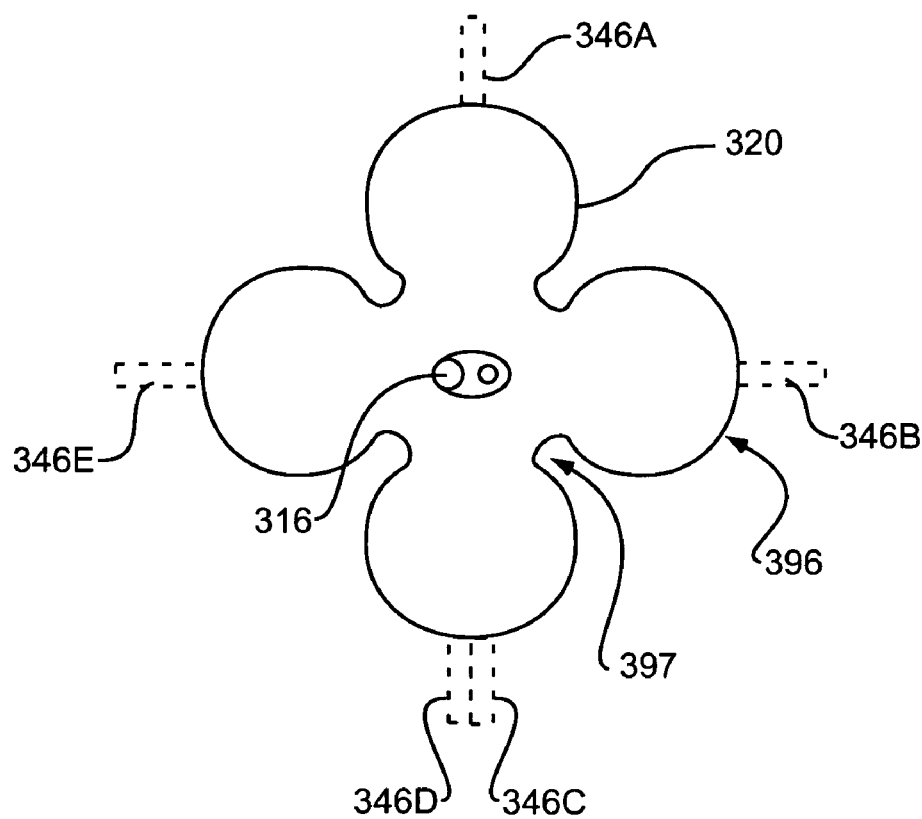
FIG. 28 shows a cross-section through line A-A' of the balloon of FIG. 27.

FIG. 28 shows a cross-section through line A-A' of FIG. 27. Balloon 320, in this embodiment has a lobed circumferential profile. Balloon 20 of catheter assembly 10 may, in another embodiment, has a similar lobed profile. The lobed profile reduces the balloon to blood vessel contact area when balloon 320 is inflated to a diameter equivalent to an inner diameter of a blood vessel. The reduction in contact may reduce blood vessel injury. The lobed profile also provides at least one perfusion pathway to allow fluid flow around and over balloon 320. By providing for fluid (e.g., blood flow) around inflated balloon 320, a catheter assembly may be retained with balloon 320 inflated at a treatment site, with a reduced risk of damage to downstream tissue then if balloon 320 completely blocked fluid flow.

As illustrated in FIG. 28, balloon 320 includes a number of side sections including lobe sections 396 separated by cusp sections 397. Lobe sections 396 may have a variety of shapes. In one embodiment, each of lobe sections 396 includes a rounded projection portion with a curved shape. In one embodiment, balloon 320 includes two, three, four, or more lobe sections 396 and two, three, four or more corresponding cusp sections. In one embodiment, balloon 320 deflates with folds (plications) along a line (length) of each cusp section 397. When deflated, balloon 320 resembles a configuration of deflated wings (e.g., four deflated wings). Deflating balloon 320 causes each lobe section 396 to deflate with a fold (plication) corresponding to a wing tip along the line at the center of each lobe section 396 so that cusp sections 397 collapse radially inward and the walls of lobe sections 396 collapse together to form folded wings. Representatively, balloon 320 may have a smaller diameter when deflated than a deflated diameter of a balloon of similar length and inflation diameter with a generally cylindrical continuous working length.

FIG. 28 shows a number of needles (needles 346A, 346B, 346C, 346D, and 346E) extending from balloon 320. In one embodiment, a catheter assembly may include one or more needles such as described above with reference to needle assembly 10. In this embodiment, each lobe section 396 of balloon 320 may have a delivery cannula connected thereto to allow a needle to be delivered to a region of interest. FIG. 28 shows needle 346C and needle 346D adjacent one another on a single lobe section 396. Such a configuration may be contemplated where, for example, it is intended that a component delivered from needle 346C combine or mix with a component delivered from needle 346D at a treatment site.

Figure 29:
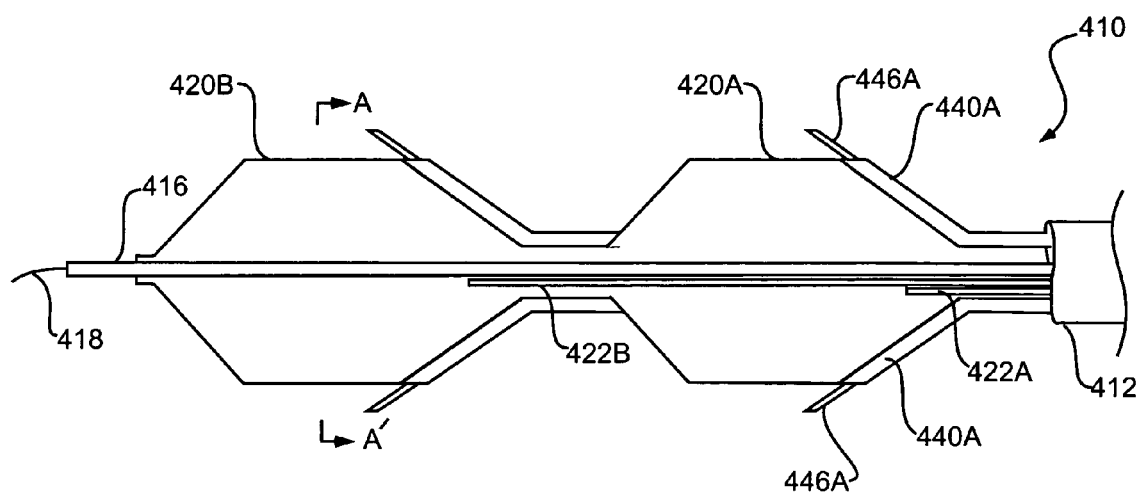
FIG. 29 shows a side view of a distal portion of an embodiment of a catheter assembly including two balloons positioned in series.

In one embodiment, a catheter assembly such as catheter assembly 10 includes a number of balloons (e.g., two or more) positioned in series or tandem to one another. Including more than one balloon may allow for multiple injections at multiple target sites along a particular vessel. Additionally, including more than one balloon increases injection coverage length and reduces the number of balloon movement for making multiple injections along the vessel. FIG. 29 illustrates an embodiment of a catheter assembly including two balloons positioned in series. FIG. 29 shows a distal portion of catheter assembly 410. The distal portion of catheter assembly 410 includes two balloons 420A and 420B positioned in series, sometimes referred to as a "tandem balloon" configuration. Except for the tandem balloon system, catheter assembly 410 as shown in FIG. 29 may include all of the features discussed above for catheter assembly 10 (see FIGS. 1-23 and the accompanying text).

As illustrated in FIG. 29, catheter assembly 410 is defined by elongated catheter body or shaft 412. Catheter assembly 410 may also include guidewire cannula 416 for allowing catheter assembly 410 to be fed and maneuvered over guidewire 418. Catheter assembly 410 includes distal balloon 420B and proximal balloon 420A separated by a distance of, for example, one to 20 mm. Distal balloon 420B and proximal balloon 420A may share the same inflation cannulas or may have separate inflation cannulas (e.g., inflation cannula 42A for proximal balloon 420A and inflation cannula 422B for distal balloon 420B). The inflation cannula (or cannulas) may be connected to an inflation port (or inflation ports) at a proximal end of catheter assembly 410. In another embodiment, balloon 420A and balloon 420B may have different diameters (e.g., distal balloon smaller) and/or different shapes.

Catheter assembly 410 may include a delivery cannula or a number of delivery cannulas disposed about the periphery of each of distal balloon 420B and/or proximal balloon 420A. Each of delivery cannula includes lumen therethrough having dimensions suitable to accommodate a needle. In one embodiment, catheter assembly 410 includes four needles, two peripherally disposed about distal balloon 420B and two peripherally disposed about proximal balloon 420A. FIG. 19 shows two delivery cannulas 440A connected to balloon 420A (a proximal taper wall of balloon 420A) and two delivery cannulas 440B connected to balloon 420B. Needles 446B peripherally disposed about distal balloon 420B are spaced either radially and/or circumferentially from each other, for example, between 45° and 180° apart. Similarly, needles 446A peripherally disposed about proximal balloon 420A are spaced either radially and/or circumferentially from each other, for example, between 45° and 180° apart. In one embodiment, needles 446A and 446B are in fluid communication with a common source supply of a therapeutic substance or treatment agent. Each of delivery assemblies is, therefore, capable of injecting the same therapeutic substance (treatment agent) or the same combination of therapeutic substances (treatment agent). In another embodiment, each needle is in fluid communication with an individual source supply of a therapeutic substance. Each needle can inject the same or different therapeutic substance. Beneficially, in the alternative example, if an interruption of the flow of a therapeutic substance (a treatment agent) occurs, the flow of a different therapeutic substance (treatment agent) to each of the other needles continues uninterrupted.

Figure 30:
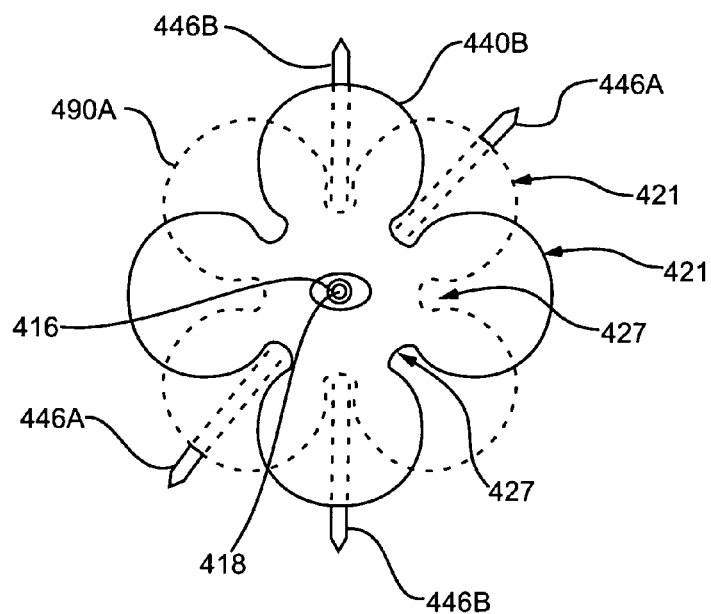
FIG. 30 shows a cross-sectional view of the catheter assembly of FIG. 29 through line A-A'.

FIG. 30 shows a cross-sectional side view through line A-A' of FIG. 29. In one embodiment, both of distal balloon 420B and proximal balloon 420A have lobed circumferential profiles. Each of distal balloon 420B and proximal balloon 420A thus includes a plurality of lobe sections 421 and cusp sections 427. Additionally, distal balloon 420B and proximal balloon 420A are positioned in a staggered arrangement as illustrated cross-sectionally in FIG. 30. In this arrangement, one lobe section 421 from one balloon is in alignment with one cusp section 427 from another balloon. The staggering arrangement allows delivery cannulas 440B peripherally disposed about distal balloon 420B to extend between lobe sections 421 of proximal balloon 420A to reach distal balloon 420B. Delivery cannulas 440A peripherally disposed about proximal balloon 420A can be positioned similarly to that of catheter assembly 10 previously described. In one embodiment, lobe sections 421 of distal balloon 420B are in alignment with cusp section 427. Thus, each delivery cannula 440B for distal balloon 420B extends from catheter body 412, extends through proximal balloon 420A by running between cusp section 427 of proximal balloon 420A (and on the outer surface of proximal balloon 420A), and connects to lobe section 421 of distal balloon 420B. In this embodiment, delivery cannulas 440B for distal balloon 420B do not extend through a body of proximal balloon 420A to reach distal balloon 420B. Delivery cannulas 440B thus extend through proximal balloon 420A on the outer surface of proximal balloon 420A by traveling through cusp section 427 of proximal balloon 420A.

Figure 31:
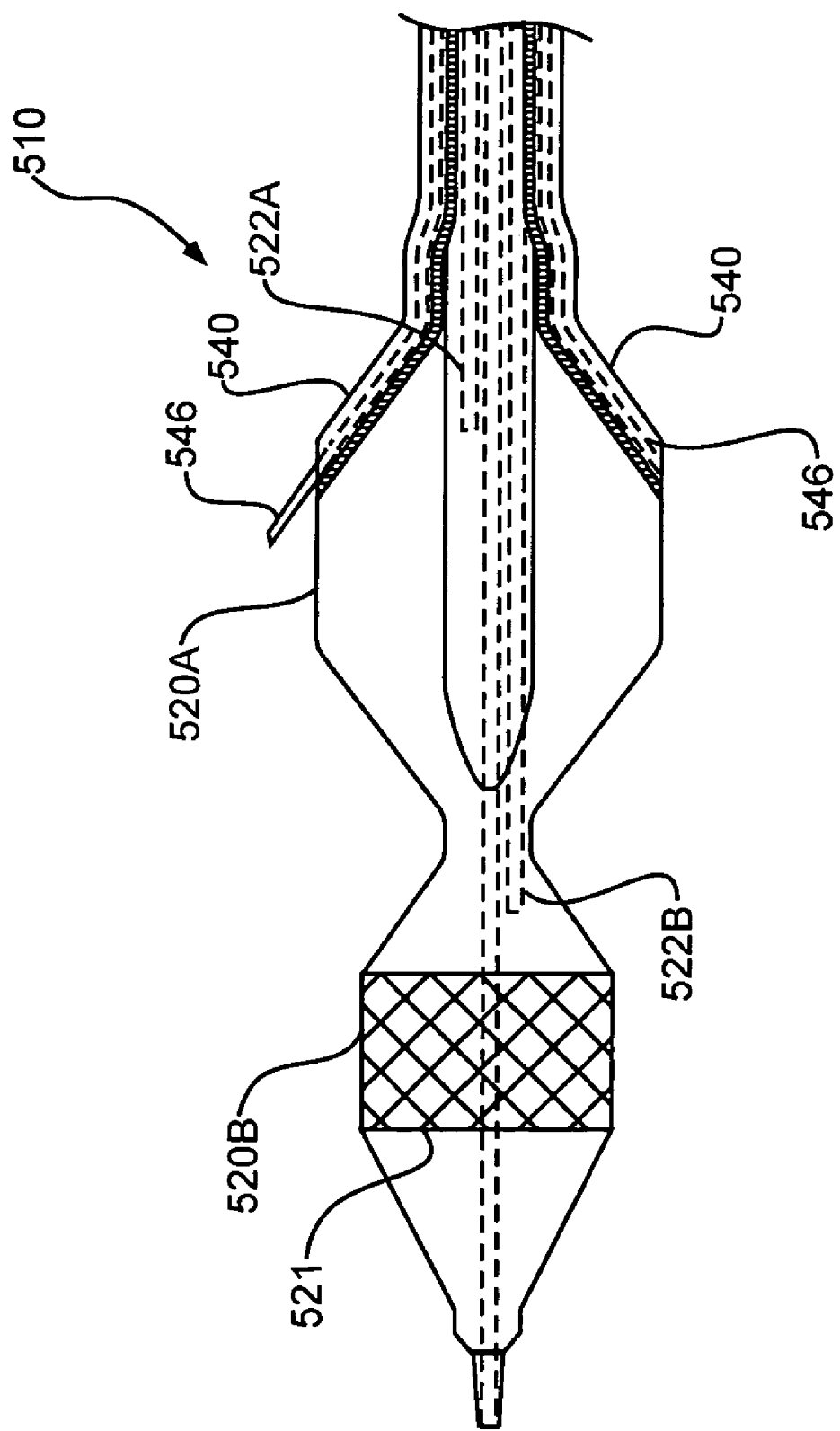
FIG. 31 shows a side view of a distal portion of another embodiment of a catheter assembly including two balloons positioned in series.

A catheter assembly much like catheter assembly 310 can have one balloon with a circular circumferential profile and one balloon with a lobed circumferential profile. FIG. 31 shows another embodiment of a catheter assembly including tandem balloons. Referring to FIG. 31, in one embodiment, catheter assembly 510 includes proximal balloon 520A having a lobed circumferential profile and distal balloon 520B having a circular profile. Catheter assembly 510 is similar to catheter assembly 10 in most aspects except that catheter assembly 510 includes separate inflation cannulas, one for each of the balloons. Catheter assembly 510 includes an inflation cannula 522A for proximal balloon 520A and inflation cannula 522B for distal balloon 520B. In one embodiment, distal balloon 520B can be a dilatation balloon or a stent delivery balloon. As shown in FIG. 31, stent 521 is disposed about distal balloon 520B. Proximal balloon 520A may be used to deliver a treatment agent or treatment agents to a region of interest such as by providing a platform for one or more delivery cannulas 540 and needles 546 (two shown).

In the preceding paragraphs, various embodiments of catheter assemblies are presented including expandable bodies described as various balloon configurations. It is appreciated that, at least to the extent the expandable body serves to locate a delivery cannula and needle, other expandable bodies are also suitable. Such other expandable bodies include metal or polymeric cages of expandable material (e.g., nitinol) or that may be expanded by a physical force on the catheter (e.g., a distally applied force causing a braided cage configuration to expand or contract). Stent like expandable bodies are also suitable.

With respect to the various embodiments presented, one or more features are described including a sheath ring disposed about a delivery cannula, proximal and distal needle stops, proximal and distal needle orientation restricters, needle material and shapes, multiple balloon configurations, etc. It is appreciated that these features may be used individually or multiple features may be used collectively depending on the requirements of the particular application.

In the preceding paragraphs, specific embodiments are described. It will, however, be evident that various modifications and changes may be made thereto without departing from the broader spirit and scope of the claims. The specification and drawings are, accordingly, to be regarded in an illustrative rather than a restrictive sense.

What is claimed is:

1. An apparatus comprising:
    an expandable body having dimensions suitable for percutaneous delivery;
    at least one delivery cannula having a lumen therethrough coupled to an exterior portion of the expandable body;
    a needle disposed in the lumen of the at least one delivery cannula, the needle comprising a body portion having a protuberance thereon and a delivery end distal to the protuberance;
    a first stop disposed in the lumen of the at least one delivery cannula at a position distal to the protuberance on the needle, the stop defining a diameter of the lumen less than an outer diameter of the needle at the protuberance; and
    a second stop disposed in the lumen of the at least one delivery cannula at a position proximal to the protuberance on the needle, the second stop defining a diameter of the lumen less than an outer diameter of the needle at the protuberance,
    wherein the first stop comprises a sleeve having an outer dimension less than a dimension of the lumen of the at least one delivery cannula and a lumen therethrough having an inner dimension greater than an outer dimension of the needle at a point other than a point of the protrusion, and
    wherein the sleeve comprises a first sleeve and the protuberance comprises a second sleeve coupled to the needle, the second sleeve having an outer dimension comprising a first cross-sectional shape of the at least one delivery cannula at a portion distal to the second stop that is different from a shape of the delivery cannula proximal to the second stop.

2. The apparatus of claim 1, wherein the first cross-sectional shape is other than circular.

3. The apparatus of claim 2, further comprising a ribbon disposed in the lumen and extending between the first stop and the second stop, the ribbon modifying a shape of the lumen, wherein the first cross-sectional shape comprises a shape corresponding to the modified shape of the lumen in the presence of the ribbon.

4. An apparatus comprising:
    an expandable body having dimensions suitable for percutaneous delivery;
    at least one delivery cannula having a lumen therethrough coupled to an exterior portion of the expandable body;
    a needle disposed in the lumen of the at least one delivery cannula, the needle comprising a body portion having a protuberance thereon and a delivery end distal to the protuberance;
    a first stop disposed in the lumen of the at least one delivery cannula at a position distal to the protuberance on the needle, the stop defining a diameter of the lumen less than an outer diameter of the needle at the protuberance;
    a second stop disposed in the lumen of the at least one delivery cannula at a position proximal to the protuberance on the needle, the second stop defining a diameter of the lumen less than an outer diameter of the needle at the protuberance;
    a catheter body having a lumen therethrough, the lumen comprising a dimension at a distal end to contain the at least one delivery cannula and a dimension at a proximal end to contain the needle; and
    a hub coupled to a proximal end of the catheter body, wherein the needle extends through the hub and is maintained in a prescribed radial orientation.

5. The apparatus of claim 4, wherein the protuberance comprises a sleeve coupled to the needle.

6. The apparatus of claim 4, wherein the protuberance comprises a first protuberance, the apparatus further comprising:

a second protuberance coupled to the needle at a portion within the hub, the second protuberance having dimensions such that the needle may move a prescribed distance within the hub.

7. The apparatus of claim 6, wherein the coupling of the second protuberance to the needle defines the prescribed orientation of the needle.

8. The apparatus of claim 6, wherein the needle has a first axial orientation with respect to a distal end of the hub and a different second axial orientation with respect to a proximal end of the hub.

9. The apparatus of claim 8, wherein the difference between the first axial orientation and the second axial orientation defines an angle of at least 15°.

10. An apparatus comprising:
an expandable body having dimensions suitable for percutaneous delivery;
at least one delivery cannula having a lumen therethrough coupled to an exterior portion of the expandable body;
a needle disposed in the lumen of the at least one delivery cannula, the needle comprising a body portion having a protuberance thereon and a delivery end distal to the protuberance;
a first stop disposed in the lumen of the at least one delivery cannula at a position distal to the protuberance on the needle, the stop defining a diameter of the lumen less than an outer diameter of the needle at the protuberance;
a second stop disposed in the lumen of the at least one delivery cannula at a position proximal to the protuberance on the needle, the second stop defining a diameter of the lumen less than an outer diameter of the needle at the protuberance,
wherein the first stop comprises a sleeve having an outer dimension less than a dimension of the lumen of the at least one delivery cannula and a lumen therethrough having an inner dimension greater than an outer dimension of the needle at a point other than a point of the protrusion, and
wherein the sleeve comprises a first sleeve and the protuberance comprises a second sleeve coupled to the needle, the second sleeve having an outer dimension comprising a first cross-sectional shape of the at least one delivery cannula at a portion proximal to the second stop that is different from a second cross-sectional shape distal to the second stop.

11. The apparatus of claim 10, wherein the protuberance comprises a sleeve coupled to the needle.

12. The apparatus of claim 10, wherein the first cross-sectional shape is other than circular.

13. The apparatus of claim 12, further comprising a ribbon disposed in the lumen and extending between the first stop and the second stop, the ribbon modifying a shape of the lumen, wherein the first cross-sectional shape comprises a shape corresponding to the modified shape of the lumen in the presence of the ribbon, and the second cross-sectional shape comprises a circular shape.

14. An apparatus comprising:
an expandable body having dimensions suitable for percutaneous delivery;
at least one delivery cannula having a lumen therethrough coupled to an exterior portion of the expandable body;
a needle disposed in the lumen of the at least one delivery cannula, the needle comprising a body portion having a protuberance thereon;
a first stop disposed in the lumen of the at least one delivery cannula at a position proximal to the protuberance on the needle, the stop defining a diameter of the lumen less than an outer diameter of the needle at the protuberance;
a second stop disposed in the lumen of the delivery cannula at a position distal to the protuberance on the needle, the second stop defining a diameter of the lumen less than an outer diameter of the needle at the protuberance;
a catheter body having a lumen therethrough, the lumen comprising a dimension at a distal end to contain the at least one delivery cannula and a dimension at a proximal end to contain the needle; and
a hub coupled to a proximal end of the catheter body,
wherein the stop comprises a sleeve having an outer dimension less than a dimension of the lumen of the at least one delivery cannula and a lumen therethrough having an inner dimension greater than an outer dimension of the needle at a point other than a point of the protrusion,
wherein the needle extends through the hub and is maintained in a prescribed radial orientation.

15. The apparatus of claim 14, wherein the protuberance comprises a first protuberance, the apparatus further comprising:
a second protuberance coupled to the needle at a portion within the hub, the second protuberance having dimensions such that the needle may move a prescribed distance within the hub.

16. The apparatus of claim 15, wherein the coupling of the second protuberance to the needle defines the prescribed orientation of the needle.

17. The apparatus of claim 14, wherein the needle has a first axial orientation with respect to a distal end of the hub and a different second axial orientation with respect to a proximal end of the hub.

18. The apparatus of claim 17, wherein the difference between the first axial orientation and the second axial orientation defines an angle of at least 15°.

19. An apparatus comprising:
a catheter cannula having a length suitable for tracking through a portion of a vasculature and a dimension suitable for percutaneous delivery;
a first needle and a second needle extending through a portion of the catheter cannula and having a distal end; and
a hub coupled to a proximal portion of the catheter cannula; and
a first protuberance coupled to the first needle and a second protuberance coupled to the second needle,
wherein the first needle and the second needle are associated with the hub such that a proximal or a distal movement of either needle within the hub is limited by contact between the protuberance and the hub,
wherein the hub comprises a first track and a second track, the first track having dimensions suitable to accommodate the first needle therein and the second track having dimensions suitable to accommodate the second needle therein, and
wherein a proximal portion of each of the first needle and the second needle is associated with the hub according to a prescribed radial orientation.

20. The apparatus of claim 19, wherein the first track comprises a first portion and a second portion, wherein the first portion has a dimension greater than the second dimension such that the portion of the first needle comprising the protuberance may advance in distal or proximal direction within the first portion.

21. The apparatus of claim 20, wherein the second portion of the first track has a dimension less than a dimension of the protuberance.

22. An apparatus comprising:
- a balloon catheter comprising a cannula having a length suitable for tracking through a portion of a vasculature and an inflatable balloon coupled to the distal end of the catheter;
- at least one needle having a length suitable for delivering a distal end to the balloon with a proximal end outside the vasculature, the needle comprising a first protuberance on a distal portion that increases an outer diameter of the at least one needle at a point of the first protuberance;
- a hub coupled to a proximal portion of the cannula and retaining the at least one needle according to a prescribed radial orientation by a second protuberance on a proximal portion of the needle;
- at least one needle cannula comprising a proximal portion and a distal portion, the needle cannula having a lumen suitable for containing the at least one needle, wherein a distal point of the lumen of the at least one catheter cannula comprises a diameter less than an exterior diameter of the at least one needle at the point of the first protuberance; and
- at least one delivery cannula different from the at least one needle cannula and coupled to a proximal portion of the balloon, and having a length dimension suitable for containing at least a portion of the length of the at least one needle, wherein proximally to distally, the at least one needle is disposed through the at least one needle cannula and the at least one delivery cannula.

23. The apparatus of claim 22, further comprising a sheath ring disposed about the at least one delivery cannula proximal to a plication region of the at least one delivery cannula defined in response to an inflation of the balloon.

24. The apparatus of claim 23, wherein the point of the lumen of the at least one catheter cannula comprising a diameter less than an exterior diameter of the at least one needle at the point of the first protuberance is a first point, the lumen of the at least one catheter cannula comprising a second point comprising a diameter less than an exterior diameter of the at least one needle at the point of the first protuberance, and wherein a distance between the first point and the second point defines a travel distance for the at least one needle.

25. The apparatus of claim 22, wherein a cross-sectional shape of at least one of the first protuberance and the needle at the point of the first protuberance is different than a cross-sectional shape of the lumen of the catheter cannula at a point at least one of proximal or distal to the point of the first protuberance.

26. The apparatus of claim 22, wherein the at least one needle is associated with the hub such that a proximal or a distal movement of the at least one needle within the hub is limited by contact between the second protuberance and the hub.

27. The apparatus of claim 22, wherein a distal portion of the at least one needle comprises a superelastic material.

* * * * *